(12) United States Patent
Mangelsdorf et al.

(10) Patent No.: US 7,501,487 B1
(45) Date of Patent: Mar. 10, 2009

(54) RETINOID RECEPTOR COMPOSITIONS AND METHODS

(75) Inventors: David J. Mangelsdorf, San Diego, CA (US); Ronald M. Evans, La Jolla, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 08/467,543

(22) Filed: Jun. 5, 1995

Related U.S. Application Data

(63) Continuation of application No. 08/336,408, filed on Nov. 8, 1994, now Pat. No. 5,723,329, which is a continuation of application No. 07/933,453, filed on Aug. 21, 1992, now abandoned, which is a continuation of application No. 07/478,071, filed on Feb. 9, 1990, now abandoned, and a continuation of application No. PCT/US91/00399, filed on Jan. 22, 1991.

(51) Int. Cl.
A07K 14/00 (2006.01)
(52) U.S. Cl. .................................................. 530/350
(58) Field of Classification Search .................. 435/7.1, 435/65.1, 65.7, 252.3, 320.1; 536/23.1, 23.5; 530/300, 350
See application file for complete search history.

(56) References Cited

U.S. PATENT DOCUMENTS

| | | | | |
|---|---|---|---|---|
| 4,880,941 A * | 11/1989 | Shroot et al. | ................... | 545/57 |
| 4,981,784 A | 1/1991 | Evans et al. | ...................... | 435/6 |
| 5,171,671 A | 12/1992 | Evans et al. | ................. | 435/69.1 |
| 5,274,077 A | 12/1993 | Evans et al. | ................. | 530/350 |
| 5,403,925 A * | 4/1995 | Ozato et al. | | |
| 5,548,063 A * | 8/1996 | Evans et al. | ................. | 530/350 |
| 5,571,692 A * | 11/1996 | Evans et al. | ................. | 435/65.1 |
| 5,571,696 A * | 11/1996 | Evans et al. | ................. | 435/65.1 |
| 6,635,429 B1 * | 10/2003 | Leid et al. | ..................... | 435/7.1 |

FOREIGN PATENT DOCUMENTS

| EP | 0 325 849 A2 | 8/1989 |
|---|---|---|
| WO | WO91/12258 | 8/1991 |

OTHER PUBLICATIONS

George et al. 1988 In Macromolecular Sequencing and Synthesis Schlesinger (ed). Alan R Liss, NY pp. 127-149.*
Wallace et al. (1987) 152 : 432-442, 1987.*
Benbrook et al., "A new retinoic acid receptor identified from a hepatocellular carcinoma" *Nature* 333:669-672 (1988).
Brand et al., "Identification of a second human retinoic acid receptor" *Nature* 332:850-853 (1988).
Chomczynski and Sacchi. "Single-Step Method of RNA Isolation by Acid Guanidinium Thiocyanate-Phenol-Chloroform Extraction" *Anal. Biochem.* 162:156-159 (1987).
Devereux et al., "A comprehensive set of sequence analysis programs for the VAX" *Nucl. Acids Res.* 12(1):387-395 (1984).
Evans, R. M., "The Steroid and Tryroid Hormone Receptor Superfamily" *Science* 240:889-895 (1988).
Gieuere et al., "Identification of a receptor for the morphogen retinoic acid" *Nature* 330:624-629 (1987).
Gieuere et al., "Identification of a new class of steroid hormone receptors" *Nature* 331:91-94 (1988).
Gieuere et al., "Spatial and temporal expression of the retinoic acid receptor in the regenerationg amphibian limb" *Nature* 337:556-569 (1989).
Giguere et al., "Functional Domains of the Human Glucocorticoid Receptor" *Cell* 46:645-652 (1986).
Glass et al., "The Thyroid Hormone Receptor Binds with Opposite Transcriptional effects to a Common Sequence Motif in Throid Hormone and Estrogen Response Elements" *Cell* 54:313-323 (1988).
Gorman et al., "Recombinant Genomes Which Express Chloramphenicol Acetyltransferase in Mammalian Cells" *Mol. Cell. Biol.* 2(9):1044-1051 (1982).
Green and Chambon. "Nuclear receptors enhance our understanding of transcription regulation" *Trends in Genetics* 4(11):309-314 (1988).
Hamada et al., "H-2RIIBP, a memeber of the nuclear hormone receptor superfamily that binds to both regulatory element of major histompatibility class I genes and the estrogen response element" *Proc. Natl. Acad. Sci. (USA)* 86:8289-8293 (1989).
Hazel et al., "A gene inducible by serum growth factors encodes a member of steroid and thyroid hormone receptor superfamily" *Proc. Natl. Acad. Sci. (USA)* 85:8444-8448 (1988).
Henrich et al., "A steroid/throid hormone receptor superfamily member in *Drosophila melanogaster* that shares extensive sequence similarity with a mammalian homologue" *Nulceic Acids Research* 18(14): 4143-4148 (1990).

(Continued)

*Primary Examiner*—Michael Pak
(74) *Attorney, Agent, or Firm*—Foley & Lardner LLP; Stephen E. Reiter

(57) ABSTRACT

The present invention relates to novel receptor polypeptides, which, upon interaction with certain ligands, or activation by certain compounds, modulate transcription of certain genes by binding to cognate response elements associated with promoters of such genes. The novel receptors of the invention modulate transcription in the presence of retinoid compounds.

The receptors of the present invention differ significantly from known retinoic acid receptors, in protein primary sequence and in responsiveness to exposure to various retinoids.

The invention provides DNAs encoding the novel receptors, expression vectors for expression of the receptors, cells transformed with such expression vectors, cells co-transformed with such expression vectors and with reporter vectors to monitor modulation of transcription by the receptors, and methods of using such co-transformed cells in screening for compounds which are capable, directly or indirectly, of activating the receptors.

The invention also provides nucleic acid probes for identifying DNAs which encode additional retinoid receptors of the same class as the novel receptors disclosed herein.

6 Claims, 9 Drawing Sheets

OTHER PUBLICATIONS

Hollenberg et al., "Primary structure and expression of a functional human glucocorticoid receptor cDNA" *Nature* 318:635-641 (1985).

Kliewer et al., "Retinoid X receptor-COUP-TF interactions modulate retinoic acid signaling" *Proc. Natl. Acad. Sci.* (*USA*) 89:1448-1452 (1992).

Krust et al., "A third human retinoic acid receptor, hRAR-γ" *Proc. Natl. Acad. Aci.* (*USA*) 86:5310-5314 (1989).

Mangelsdorf et al., "Nuclear receptor that indentifies a novel retinoic acid response pathway" *Nature* 345: 224-229 (1990).

Thompson and Evans. "Trans-activation by hormone receptors: Functional parallels with steroid hormone receptors" *Proc. Natl. Acad. Sci.* (*USA*) 86:3494-3498 (1989).

Umesono and Evans. "Determinants of Terget Gene Specificity for Steroid/Thyroid Hormone Receptors" *Cell* 57:1139-1146 (1989).

Umesono et al., "Retinoic acid and throid hormone induce gene expression through a common responsive element" *Nature* 336:262-265 (1988).

Weinberger et al., "The *c-erb-A* gene encodes a thyroid hormone receptor" *Nature* 324:641-646 (1986).

Zelent et al., "Cloning a murine α and β retinoic acid receptors and a novel receptor γ predominantly expressed in skin" *Nature* 339:714-717 (1989).

\* cited by examiner

RETINOID RECEPTOR COMPOSITIONS AND METHODS

RELATED APPLICATIONS

This application is a continuation of application U.S. Ser. No. 08/336,408 filed Nov. 8, 1994 U.S. Pat. No. 5,723,329, now, which is a continuation of application U.S. Ser. No. 07/933,453, filed Aug. 21, 1992, now abandoned; which is a continuing application of U.S. Ser. No. 07/478,071, filed Feb. 9, 1990, now abandoned, and PCT Serial No. US91/00399, filed Jan. 22, 1991, the entire contents of which are hereby incorporated by reference herein.

TECHNICAL FIELD

The present invention concerns novel, steroid hormone-like receptor proteins and methods of making and using same.

More particularly, the invention relates to steroid hormone-like receptor proteins with transcription-modulating effects. Such proteins are responsive to the presence of retinoic acid and other vitamin A metabolites.

BACKGROUND OF THE INVENTION

The retinoids comprise a group of compounds including retinoic acid, retinol (vitamin A), and a series of natural and synthetic derivatives that together exert profound effects on development and differentiation in a wide variety of systems. Although early studies focused on the effects of retinoids on growth and differentiation of epithelial cells, their actions have been shown to be widespread. Many recent studies have examined the effects of these molecules on a variety of cultured neoplastic cell types, including the human promyelocytic leukemia cell line, HL60, where retinoic acid appears to be a potent inducer of granulocyte differentiation. In F9 embryonal carcinoma cells, retinoic acid will induce the differentiation of parietal endoderm, characteristic of a late mouse blastocyst. Retinoic acid also appears to play an important role in defining spatio-temporal axes in the developing avian limb and the regenerating amphibian limb.

Retinoic acid has been shown to induce the transcription of several cDNAs whose gene products have been isolated by differential screening. This observation supports the hypothesis that retinoic acid exerts its action via modulation of gene expression, in a manner analogous to the way in which steroid and thyroid hormones influence their target genes.

The ability to identify compounds which affect transcription of genes which are responsive to retinoic acid or other metabolites of vitamin A, would be of significant value, e.g., for therapeutic applications. Further, systems useful for monitoring solutions, body fluids and the like for the presence of retinoic acid, vitamin A or metabolites of the latter would be of value in various analytical biochemical applications and, potentially, medical diagnosis.

Through molecular cloning studies it has been possible to demonstrate that receptors for steroid, retinoid and thyroid hormones are all structurally related. These receptors comprise a superfamily of regulatory proteins that are capable of modulating specific gene expression in response to hormone stimulation by binding directly to cis-acting elements (Evans, Science 240, 889 (1988); Green and Chambon, Trends genet. 4, 309 (1988)). Structural comparisons and functional studies with mutant receptors have established that these molecules are composed of discrete functional domains, most notably, a DNA-binding domain that is composed typically of 66-68 amino acids (including two zinc fingers), and an associated carboxy terminal stretch of approximately 250 amino acids which comprises the ligand-binding domain (reviewed in Evans, supra).

Low-stringency hybridization has permitted the isolation and subsequent delineation of a growing list of gene products which possess the structural features of hormone receptors.

Recently, a retinoic acid dependent transcription factor, referred to as RAR-alpha (retinoic acid receptor-alpha), has been identified. Subsequently, two additional RAR-related genes have been isolated; thus there are now at least three different RAR subtypes (alpha, beta and gamma) known to exist in mice and humans. These retinoic acid receptors (RARs) share homology with the superfamily of steroid hormone and thyroid hormone receptors and have been shown to regulate specific gene expression by a similar ligand-dependent mechanism (Umesono et al., Nature 336, 262 (1988)). These RAR subtypes are expressed in distinct patterns throughout development and in the mature organism.

Other information helpful in the understanding and practice of the present invention can be found in commonly assigned, co-pending U.S. patent application Ser. Nos. 108, 471, filed Oct. 20, 1987; 276,536, filed Nov. 30, 1988; 325, 240, filed Mar. 17, 1989; 370,407, filed Jun. 22, 1989; and 438,757, filed Nov. 16, 1989, all of which are hereby incorporated herein by reference in their entirety.

SUMMARY OF THE INVENTION

We have discovered novel receptors which are activated to modulate transcription of certain genes in animal cells, when the cells are exposed to retinoids, such as retinoic acid and retinal. The novel receptors differ significantly from known retinoic acid receptors, both in terms of the primary protein sequence and responsiveness to various retinoids.

The novel receptors have several isoforms located at genetically distinct loci. They are capable of transactivating through cis elements similar to retinoic acid receptors, but show a different rank potency and dose dependency to retinoids. Northern analyses of the novel receptors of the present invention indicate that each isoform has a unique pattern of expression in adult tissue and is temporally and spatially expressed in the embryo. Binding experiments demonstrate that the novel receptor proteins have a low affinity for [$^3$H] retinoic acid. These results, taken together with results from transactivation studies, suggest the ligand(s) for the novel receptors is a metabolite(s) or structural analog(s) of retinoic acid. The invention provides DNAs encoding novel receptors, expression vectors for expression of the receptors, cells transformed with such expression vectors, cells co-transformed with such expression vectors and reporter vectors to monitor modulation of transcription by the receptors, and methods of using such co-transformed cells in screening for compounds which are capable, directly or indirectly, of activating the receptors.

The invention also provides single-stranded nucleic acid probes for identifying DNAs encoding additional retinoid receptors.

The invention also provides a method for making the receptors of the invention by expressing DNAs which encode the receptors in suitable host organisms.

Animal cells in which receptors of the invention are present can be employed to assay fluids for the presence of retinoids. Animal cells of the invention can also be employed to screen compounds of potential therapeutic value for their ability to bind and/or promote trans-activation (i.e., trans-acting transcriptional activation) by the receptors of the invention.

As will be described in greater detail below, the receptors of the invention modulate transcription of genes. This occurs upon binding of receptor to hormone response elements, which are positioned operatively, with respect to promoters for such genes, for such modulation to occur. Among hormone response elements contemplated for use in the practice of the present invention are $TRE_p$, the beta-retinoic acid response element, and the estrogen response element, as well as closely related elements which are disclosed, for example, in application Ser. No. 438,757, filed Nov. 16, 1989, and application Ser. No. 325,240, filed Mar. 17, 1989.

DETAILED DESCRIPTION OF THE INVENTION

Figure 1:
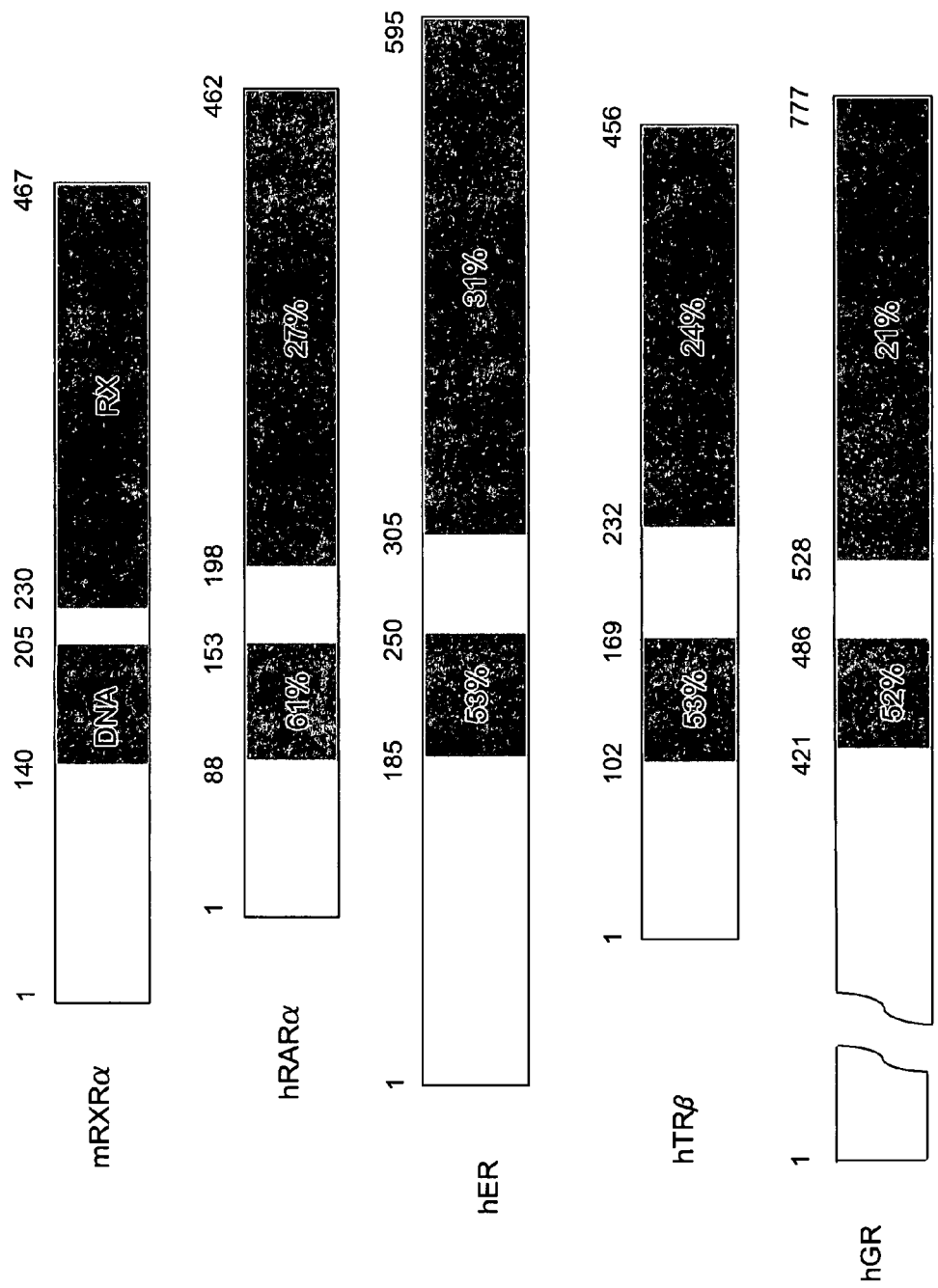
FIG. 1 shows the extent of amino acid identity (i.e., "homology") between the DNA binding domain ("DNA") and ligand binding domain ("RX") of mouse RXR-alpha (mRXRα), relative to the corresponding domains of human retinoic acid receptor-alpha (hRARα), human estrogen receptor (hER), human thyroid hormone receptor-beta (hTRβ) and human glucocorticoid receptor (hGR).

The invention concerns novel polypeptides, which are characterized by:
(1) being responsive to the presence of retinoid(s) to regulate transcription of associated gene(s);
(2) having a DNA binding domain of about 66 amino acids with 9 Cys residues, wherein said DNA binding domain has:
    (a) less than about 65% amino acid identity with the DNA binding domain of hRAR-alpha,
    (b) less than about 55% amino acid identity with the DNA binding domain of hTR-beta, and
    (c) less than about 55% amino acid identity with the DNA binding domain of hGR; and
(3) not including the sequence set forth in Sequence ID No 7.

The novel polypeptide receptors of the present invention can be further characterized in a variety of ways, e.g., by increasing the rate of transcription of a target gene in a construct comprising a promoter operatively linked to a hormone response element for transcriptional activation by said receptors, relative to the rate of transcription in the absence of said receptor and/or in the absence of retinoic acid and retinal. Transcription of said target gene is measured in an animal cell in culture, the medium of which comprises retinoic acid or retinal at a concentration greater than about $5 \times 10^{-7}$ M.

Alternatively, the polypeptide receptors of the present invention can be further characterized as being encoded by a continuous nucleotide sequence which encodes substantially the same amino acid sequence as that of amino acids 1-462 shown in Sequence ID No. 2 [hRXRα], amino acids 1-467 shown in Sequence ID No. 4 [mRXRα], or amino acids 1-463 shown in Sequence ID No. 6 [mRXRγ].

As yet another alternative, the polypeptide receptors of the present invention can be characterized as being encoded by a continuous nucleotide sequence which encodes substantially the same amino acid sequence as that of amino acids 135-200 shown in Sequence ID No. 2 [DNA binding domain of hRXRα], amino acids 140-205 shown in Sequence ID No. 4 [DNA binding domain of mRXRα], or amino acids 139-204 shown in Sequence ID No. 6 [DNA binding domain of mRXRγ].

As still another alternative, the polypeptide receptor of the present invention can be characterized as being encoded by a continuous nucleotide sequence which is substantially the same as nucleotides 76-1464 shown in Sequence ID No. 1 [hRXRα], nucleotides 181-1581 shown in Sequence ID No. 3 [mRXRα], or nucleotides 123-1514 shown in Sequence ID No. 5 [mRXRγ].

As employed herein, the term "retinoids" refers to naturally occurring compounds with vitamin A activity synthetic analogs and various metabolites thereof. The retinoids are a class of compounds consisting of four isoprenoid units joined in head-to-tail manner. Numerous retinoids have been identified, as described, for example, by Sporn, Roberts and Goodman in the two volume treatise entitled *The Retinoids* (Academic Press, NY, 1984), to which the reader is directed for further detail. Exemplary retinoids include retinol, retinyl acetate, retinyl hexadecanoate, α-retinyl, 4,14-retroretinol, deoxyretinol, anhydroretinol, 3,4-didehydroretinol, 15,15-dimethyl retinol, retinyl methyl ether, retinyl phosphate, mannosyl retinyl phosphate, retinol thioacetate, retinal (retinaldehyde), 3,4-didehydroretinal, retinylidene acetylacetone, retinylidene-1,3-cyclopentanedione, retinal oxime, retinaldehyde acetylhydrazone, retinoic acid, 4-hydroxyretinoic acid, 4-oxoretinoic acid, 5,6-dihydroretinoic acid, 5,6-epoxyretinoic acid, 5,8-epoxyretinoic acid, the open-chain $C_{20}$ analog of retinoic acid (i.e., (all-E-3,7,11,15-tetramethyl-2,4,6,8,10, 2,14-hexadecaheptaenoic acid), 7,8-didehydroretinoic acid, 7,8-dihydroretinoic acid, "$C_{15}$ Acid" (E, E)-3-methyl-5-(2,6, 6-trimethyl-2-cyclohexen-1-yl)-2,4-pentanedioic acid), "$C_{17}$ Acid" ((E,E,E)-5-methyl-7-(2,6,6-trimethyl-1-cyclohexen -1- yl)-2,4,6-hepatrienoic acid), "$C_{22}$ Acid" (14'-apo-β, ψ-carotenoic acid), retinoic acid esters (e.g., methyl ester, ethyl ester, etc.), retinoic acid ethylamide, retinoic acid 2-hydroxyethylamide, methyl retinone, "$C_{18}$" Ketone" ((E,E, E)-6-methyl-8-(2,6,6-trimethyl- 1-cyclohexen-1-yl)-3,5,7-ocatrien-2-one), and the like.

In addition, according to the present invention, there are provided DNA sequences which encode novel polypeptides as described above.

Further in accordance with the present invention, there are provided DNA constructs which are operative in animal cells in culture to make said polypeptides.

According to a still further embodiment of the present invention, there are provided animal cells in culture which are transformed with DNA constructs (as described above), which are operative in said cells to make receptor polypeptides, by expression of DNA segments which encode the above described polypeptides.

Among the animal cells contemplated for use in the practice of the present invention are those which are further transformed with a reporter vector which comprises:
  (a) a promoter that is operable in the cell,
  (b) a hormone response element, and
  (c) a DNA segment encoding a reporter protein,
    wherein said reporter protein-encoding DNA segment is operatively linked to said promoter for transcription of said DNA segment, and
    wherein said hormone response element is operatively linked to said promoter for activation thereof.

In accordance with the present invention, there is also provided a method of testing a compound for its ability to regulate the transcription-activating properties of the above-described receptor polypeptides, which method comprises assaying for the presence or absence of reporter protein upon contacting of cells containing a reporter vector and receptor polypeptide with said compound; wherein said reporter vector and said receptor polypeptide are as described above.

In accordance with a still further embodiment of the present invention, there are provided various probes, which can be used to identify genes encoding receptors related to those of the present invention. In this regard, particular reference is made to Examples V and VI below. More particularly, the invention provides labeled, single-stranded nucleic acids comprising sequences of at least 20 contiguous bases having substantially the same sequence as any 20 or more contiguous bases selected from:
  (i) bases 2-1861, inclusive, of the DNA illustrated in Sequence ID No. 1 [hRXR-α), or
  (ii) bases 20-2095, inclusive, of the DNA illustrated in Sequence ID No. 3 (mRXR-α], or
  (iii) bases 15-1653, inclusive, of the DNA illustrated in Sequence ID No. 5 [mRXR-γ], or
  (iv) the complement of any one of the sequences according to (i), (ii), or (iii).

As employed herein, the term "labeled single-stranded nucleic acid sequences" refers to single-stranded DNA or RNA sequences which have been modified by the addition thereto of a species which renders the "labeled" sequence readily detectable from among other unmodified sequences. Exemplary labels include radioactive label (e.g., $^{32}P$, $^{35}S$), enzymatic label (e.g., biotin), and the like.

Preferred probes contemplated for use in the practice of the present invention are those having at least about 100 contiguous bases selected from the above-described sequences. Especially preferred are probes having in the range of about 198 up to several hundred nucleotides, because greater selectivity is afforded by longer sequences.

The invention also encompasses a method of making the above-described receptor polypeptides, which method comprises culturing suitable host cells which are transformed with an expression vector operable in said cells to express DNA which encodes receptor polypeptide. Suitable hosts contemplated for use in the practice of the present invention include yeast, bacteria, mammalian cells, insect cells, and the like. E. coli is the presently preferred bacterial species. Any of a number of expression vectors are well known to those skilled in the art that could be employed in the method of the invention. Among these are the prokaryotic expression vectors pNH8A, pNH16A and pNH18A available from Stratagene, La Jolla, Calif. USA.

Further information on the invention is provided in the following non-limiting examples and description of an exemplary deposit.

EXAMPLES

Example I

The KpnI/SacI restriction fragment (503 bp) including the DNA-binding domain of hRAR-alpha-encoding DNA [See Giguere et al., Nature 330, 624 (1987); and commonly assigned U.S. patent application Ser. No. 276,536, filed Nov. 30, 1988; and European Patent Application Publication No. 0 325 849, all incorporated herein by reference] was nick-translated and used to screen a lambda-gt11 human liver cDNA library (Kwok et al., Biochem. 24, 556 (1985)) at low stringency. The hybridization mixture contained 35% formamide, 1× Denhardt's, 5×SSPE (1×SSPE=0.15 M NaCl, 10 mM $Na_2HPO_4$ 1 mM EDTA), 0.1% SDS, 10% dextran sulfate, 100 mg/ml denatured salmon sperm DNA and $10^6$ cpm of [$^{32}P$]-labelled probe. Duplicate nitrocellulose filters were hybridized for 16h at 42° C., washed once at 25° C. for 15 min with 2×SSC (1×SSC=0.15 M NaCl, 0.015 M sodium citrate), 0.1% SDS and then washed twice at 55° C. for 30 min. in 2×SSC, 0.1% SDS. The filters were autoradiographed for 3 days at −70° C. using an intensifying screen.

Positive clones were isolated, subcloned into pGEM vectors (Promega, Madison, Wis., USA), restriction mapped, and re-subcloned in various sized restriction fragments into M13mp18 and M13mp19 sequencing vectors. DNA sequence was determined by the dideoxy method with Sequenase™ sequencing kit (United States Biochemical, Cleveland, Ohio, USA) and analyzed by University of Wisconsin Genetics Computer Group programs (Devereux et al., *Nucl. Acids Res.* 11,387 (1984)). A unique receptor-like sequence was identified and designated lambda-HL3-1.

Lambda-HL3-1 was used as a hybridization probe to rescreen a lambda-gt10 human kidney cDNA library (Arriza et al., Science 237, 268 (1987)) which produced several clones, the longest of which was sequenced and designated lambda-XR3-1. The DNA sequence obtained as an EcoRI-fragment from lambda-XR3-1 has the sequence indicated in Sequence ID No. 1 [hRXRα].

Similar screening of a mouse whole embryo library with the full-length hRXR-alpha clone described above provided additional sequences which encode different isoforms of the human RXR-alpha receptor. In addition, the mouse homolog (mouse RXR-alpha) was also identified in this way.

Thus, mRNA was isolated from 14.5 day post-coitus (p.c.) mouse embryos, translated into cDNA, Tinkered with EcoRI/NotI linkers, then inserted into the unique EcoRI site of the cloning vector λ-ZAP (Stratogene). The resulting library was screened at reduced stringency with $^{32}P$-labeled, full length hRXR-alpha as the probe.

The DNA sequences of the resulting clones are set forth as Sequence ID No. 3 [mRXRα] and Sequence ID No. 5 [mRXRγ].

Example II

Amino acid sequences of mRXR-alpha, hRAR-alpha (human retinoic acid receptor-alpha), hER (human estrogen receptor) hTR-beta (human thyroid hormone receptor-beta) and hGR (human glucocorticoid receptor) were aligned using the University of Wisconsin Genetics Computer Group program "Bestfit" (Devereux et al., supra). Regions of significant similarity between mRXR-alpha and the other receptors, i.e., the 66-68 amino acid DNA binding domains and the ligand-binding domains, are presented schematically in FIG. 1 as percent amino acid identity.

Similarly, the amino acid sequences of human RAR-alpha (hRARα), human RAR-beta (hRARβ), human RAR-gamma (hRARγ), human TR-beta (hTRβ) and human RXR-alpha (hRXRα) were aligned. As done in FIG. 1, regions of significant similarity between hRAR-alpha and the other receptors are presented schematically in FIG. 2 as percent amino acid identity.

Figure 3:
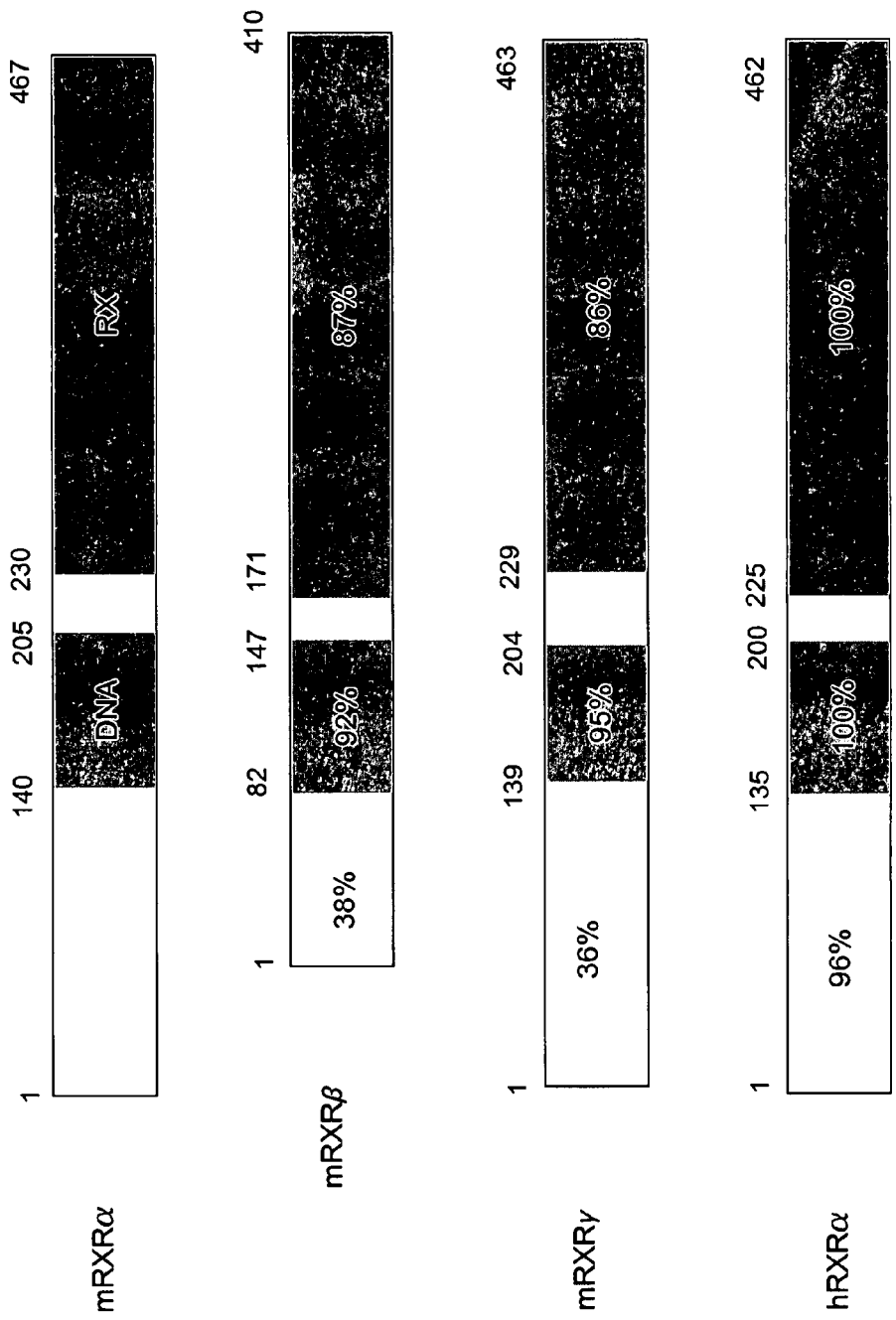
FIG. 3 shows the extent of amino acid identity (i.e., "homology") between the DNA binding domain ("DNA") and ligand binding domain ("RX") of mRXRα, relative to the corresponding domains of mouse RXR-beta (mRXRβ), mouse RXR-gamma (mRXRγ) and hRXRα.

A further comparison of receptors is set forth in FIG. 3. Thus, the amino acid sequences of mouse RXR-alpha (mRXRα), mouse RXR-beta (mRXRβ), mouse RXR-gamma (mRXRγ) and human RXR-alpha (hRXRα) were aligned, and the percent amino acid identity presented schematically in FIG. 3.

Although the DNA-binding domains of both mRXR-alpha and hRXR-alpha are conserved relatively well with respect to other receptors (such as hRAR-alpha and hTR-beta), the ligand binding domain is poorly conserved. (See FIGS. 1 and 3). A comparison between the retinoic acid receptor subfamily of receptors and hRXR-alpha reveals nothing to suggest that hRXR-alpha is related to any of the known retinoid receptors (FIG. 2).

Example III

*Drosophila melanogaster* Schneider line 2 ("S2") cells (Schneider, Embryol. Exp. Morphol. 27, 353 (1972), which are readily available, were seeded at 2×10$^6$ per 35 mm$^2$ culture dish and maintained in Schneider medium (GIBCO/Life Technologies, Inc., Grand Island, N.Y., USA) supplemented with penicillin, streptomycin and 12% heat-inactivated fetal bovine serum (Irvine Scientific, Santa Ana, Calif., USA). The cells were transiently co-transfected with 10 µg/dish of plasmid DNA by calcium phosphate precipitation (Krasnow et al., Cell 57, 1031 (1989): 4.5 µg/dish of receptor expression vector or control construct (producing no hRXR-alpha); 0.5 µg/dish of reporter plasmid or control reporter plasmid: 0.5 µg/dish of reference plasmid; and 4.5 µg inert plasmid DNA.

In the receptor expression vector, A5C-RXR-alpha (4.5 µg/dish), receptor hRXR-alpha is constitutively expressed in the S2 cells under the control of the *Drosophila* actin 5C promoter (A5C; Thummel et al., Gene 74: 445 (1988)) driving transcription of the EcoRI-site-bounded insert of lambda-XR3-1. In the control vector, A5C-RXR$_{rev}$ (also 4.5 µg/ml), the EcoRI-site-bounded insert from lambda-XR3-1 is inserted in the reverse (i.e., non-coding or non-sense-coding) orientation.

A5C-RXR-alpha was made by first inserting at the unique BamHI site of A5C a linker of sequence:

5'-GATCCGATATCCATATG<u>GAATTC</u>GGTACCA, (SEQ ID NO: 9)

and then inserting, at the EcoRI site of the linker (underlined above), the EcoRI-site-bounded insert of lambda-XR3-1 (See Example I).

The reporter plasmid ADH-TRE$_p$-CAT (at 0.5 µg/dish) contains the palindromic thyroid hormone response element TREp, having the sequence:

5'-AGGTCATGACCT (SEQ ID NO:10)

[(Glass et al. Cell 54, 313 (1988); Thompson and Evans, Proc. Natl. Acad. Sci. (USA) 86, 3494 (1989)], inserted into position –33 (with respect to the transcription start site) of a pD33-ADH-CAT background (Krasnow et al., Cell 57, 1031 (1989)).

pD33-ADH-CAT is a plasmid with the distal promoter of the *Drosophila melanogaster* alcohol dehydrogenase gene linked operably for transcription to the bacterial (*E. coli*) chloramphenicol acetyltransferase ("CAT") gene, a gene for the indicator protein CAT. ADH-TREp-CAT was made by inserting the oligonucleotide of sequence:

5'-CTAGAGGTCATGACCT (SEQ ID NO:11) TCCAG-TACTGGAGATC-5' (SEQ ID NO:12)

into the XbaI site at position –33 in pD33-ADH-CAT. pD33-ADH-CAT, without TREp, served as a control reporter (i.e., background) plasmid.

A reference plasmid encoding beta-galactosidase driven by the actin 5C promoter also was transfected (0.5 µg/dish) along with pGEM DNA (4.5 µg/dish) (Promega, Madison, Wis.) to make up the final DNA concentration to 10 µg/dish. The reference plasmid was made by inserting a BamHI-site bounded, beta-galactosidase-encoding segment into the unique BamHI site of A5C. The purpose of the reference plasmid was to normalize results for transfection efficiency.

Twenty-four hours post-transfection, various retinoids were added to the cultures. The retinoids were dissolved in dimethyl-sulfoxide and/or ethanol and the resulting solution was added to 0.1% v/v of culture medium. Initial concentration of the retinoids in the culture media was 10$^{-6}$ M, except for the experiments underlying the data displayed in FIG. 4, for which varying concentrations of retinoic acid were used.

In control runs, ethanol, at 0.1% v/v in the medium, was used in place of a solution of retinoid.

Cultures were maintained in the dark for 36 hr after addition of retinoid and then harvested. All other parts of the experiments, involving retinoids, were carried out in subdued light.

Cell lysates were centrifuged. Supernatants were assayed for beta-galactosidase, following Herbomel et al., Cell 39, 653-662 (1984), and units/ml of beta-galactosidase activity was calculated. CAT assays (normalized to beta-galactosidase activity) of supernatants were incubated for 75 unit-hours ("units" referring to units of beta-galactosidase activity), as described by Gorman et al., Mol. Cell. Biol. 2, 1044 (1982), usually 150 units for 30 minutes.

No hRXR-alpha dependent activation of CAT expression was noted in any experiment in which control reporter was used in place of ADH-TREp-CAT. Similarly, essentially no activation was observed for runs where control plasmid, A5C-hRXR$_{rev}$, was used in place of A5C-hRXR.

The induction of CAT activity in retinoid-treated cells was compared with induction in untreated (i.e., only ethanol-treated) cells. Induction was measured in the presence of retinoic acid (RA), retinal (RAL), retinol acetate (RAC), retinol (ROH), and retinol palmitate (RP). The production of chloramphenicol acetyltransferase (CAT) from the reporter vector (ADH-TREp-CAT) was measured in *Drosophila melanogaster* Schneider line 2 cells, co-trans-formed with the hRXR-alpha expression vector A5C-RXR-alpha, and exposed to a medium to which retinoic acid (RA), retinal (RAL), retinol acetate (RAC), retinol (ROH), or retinol palmitate (RP) has been added to a concentration of $10^{-6}$ M. The relative induction observed was RA>RAL>RAC>ROH>RH.

Figure 4:
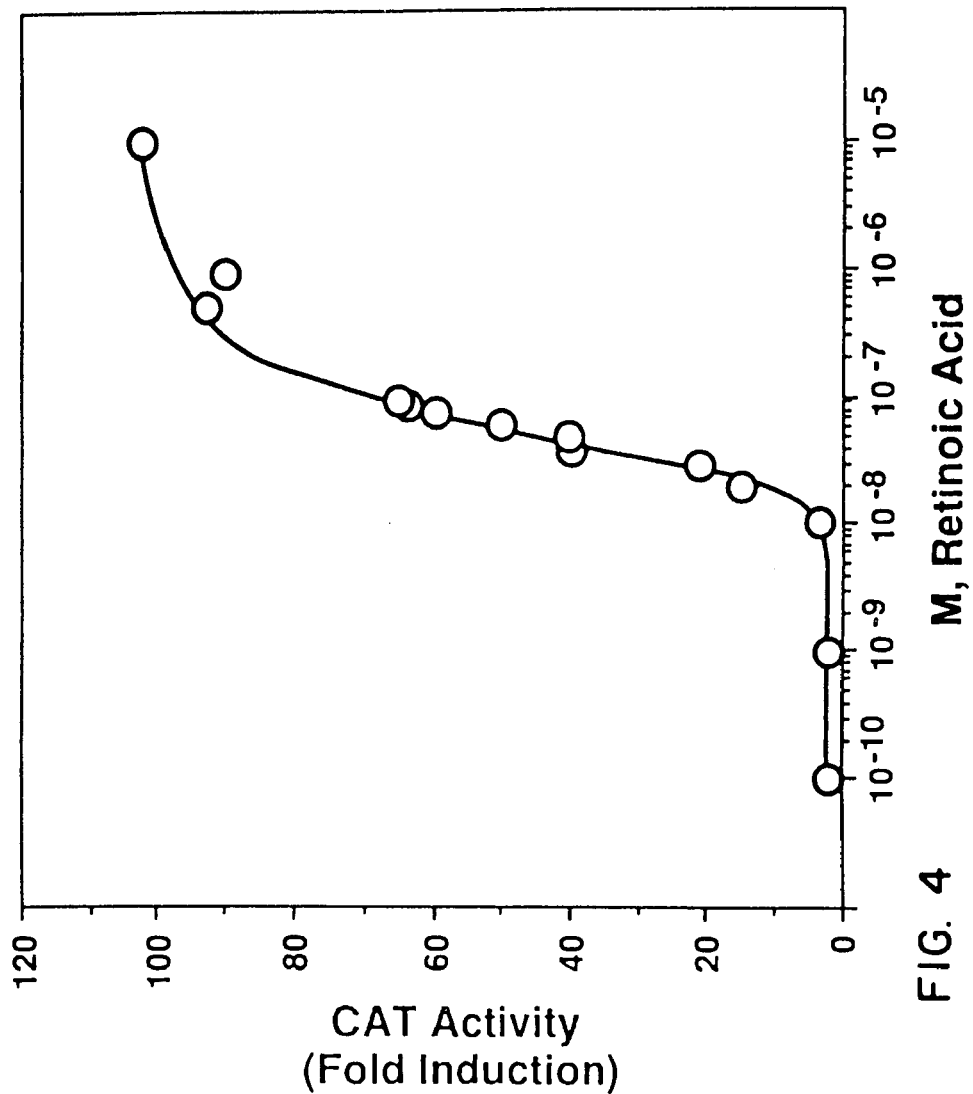
FIG. 4 illustrates the production of CAT from the reporter vector (ADH-TREp-CAT) in *Drosophila melanogaster* Schneider line 2 cells, which are co-transformed with receptor expression vector A5C-RXR-alpha and are in a medium containing various concentrations of retinoic acid.

In FIG. 4 are displayed the results, also expressed in terms of "fold-induction" of CAT activity, as described in the previous paragraph, with retinoic acid at a number of different concentrations, to show the "dose response" of hRXR-alpha (in trans-activation at TREp in insect cells) to retinoic acid in the medium of the cells.

Example IV

This example, describing experiments similar to those described in Example III, shows that hRAR-alpha and hRXR-alpha differ significantly in their properties, specifically with respect to trans-activation of transcription from promoters.

The mammalian receptor-expression vector RS-hRAR-alpha, from which hRAR-alpha is produced under control of the 5'-LTR promoter of the rous sarcoma virus proviral DNA, is described in Giguere et al., Nature 330, 624 (1987); commonly assigned U.S. patent application Ser. No. 276,536, filed Nov. 30, 1988; and European Patent Application Publication No. 0 325 849, all incorporated herein by reference.

The receptor-expression vector RS-hRXR-alpha is constructed similarly to RS-hRAR-alpha, by inserting the EcoRI-site-bounded, hRAR-alpha-encoding segment of lambda-XR3-1 into plasmid pRS (Giguere et al., Cell 46, 645 (1986)).

Control plasmid pRSns is pRS with a non-sense-coding sequence inserted in place of receptor-coding sequence.

Reporter plasmid delta-MTV-TREp-CAT, also known as TREp1MCAT, has also been described (Umesono et al., Nature 336, 262 (1988), Thompson and Evans, supra., see also Umesono and Evans, Cell 57, 1139 (1989). When a control reporter, designated delta-MTV-CAT, which is substantially delta-MTV-TREp-CAT with TREp removed, was used in place of delta-MTV-TREp-CAT, no CAT activity was found with either receptor with any of the retinoids or retinoid analogs.

Reference plasmid, RS-beta-galactosidase, is also known and is substantially the same as RS-hRAR-alpha and RS-hRXR-alpha but has a beta-galactosidase-encoding segment in place of the receptor-encoding segment.

Culture of CV-1 cells, co-transfections (with reporter plasmid, receptor-expression-plasmid or control plasmid, reference plasmid and inert plasmid DNA) and CAT assays were performed as described in Umesono et al., Nature 336, 262 (1988). Co-transfections and CAT assays were carried out by methods similar to those described in Example III. Similar to the experiments in Example III, subdued light was used.

Figure 5:
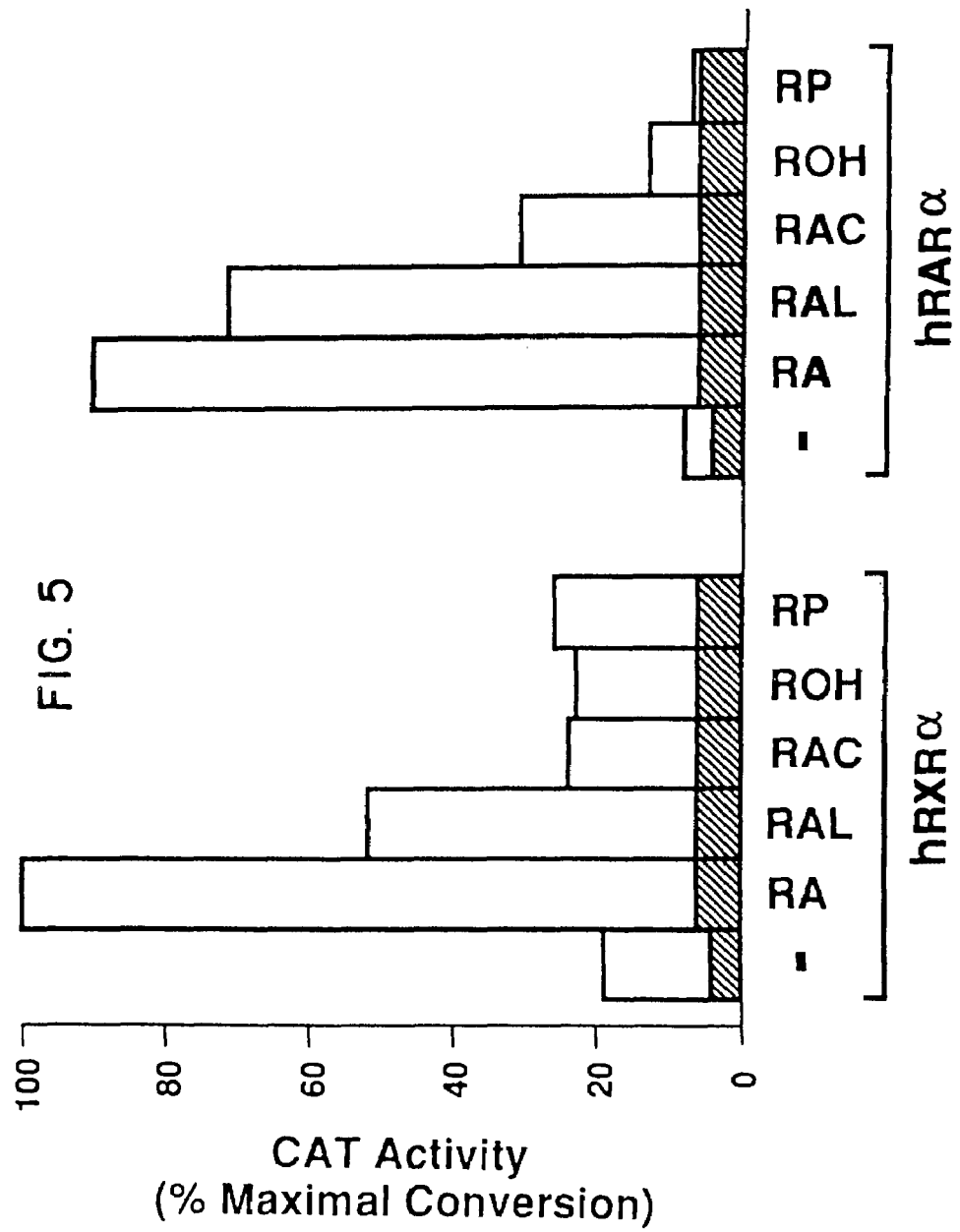
FIG. 5 illustrates the differences in transcription-activating activities of hRXR-alpha and hRAR-alpha, in mammalian cells in culture containing different vitamin A metabolites.

When CV-1 cells co-transformed with reporter plasmid (delta-MTV-TREp-CAT), reference plasmid, control plasmid (i.e., expressing no receptor), and receptor plasmid (RS-hRAR-alpha or RS-hRXR-alpha), were exposed to retinoids RA, RAL, RAC, ROH, RP, (which are naturally occurring vitamin A metabolites), or retinoid-free ethanol, the results shown in FIG. 5 were obtained. The Figure illustrates production of CAT from reporter plasmid in monkey kidney cells of the CV-1 line, which are co-transformed with hRXR-alpha-producing expression vector RS-hRXR-alpha or hRAR-alpha-producing expression vector RS-hRAR. Experiments are carried out in a medium to which RA, RAL, RAC, ROH, or RP has been added to a concentration of $10^{-6}$ M. The bars over the "−" sign indicate the levels of CAT production when the cells are exposed to no retinoid (i.e., retinoid-free ethanol). The hatched bars indicate the level of CAT production when a control expression vector, from which no receptor is expressed, is employed in place of the receptor expression vector. The open bars indicate the level of CAT production when receptor-producing expression vector is employed. In each case, the retinoids were added as ethanolic solutions, with the volume of solution 0.1% (v/v) in the medium. Retinoid-free ethanol was added to 0.1% v/v. Results are plotted as percentages of the maximal response observed in the experiments, i.e., hRXR-alpha with RA.

Figure 6:
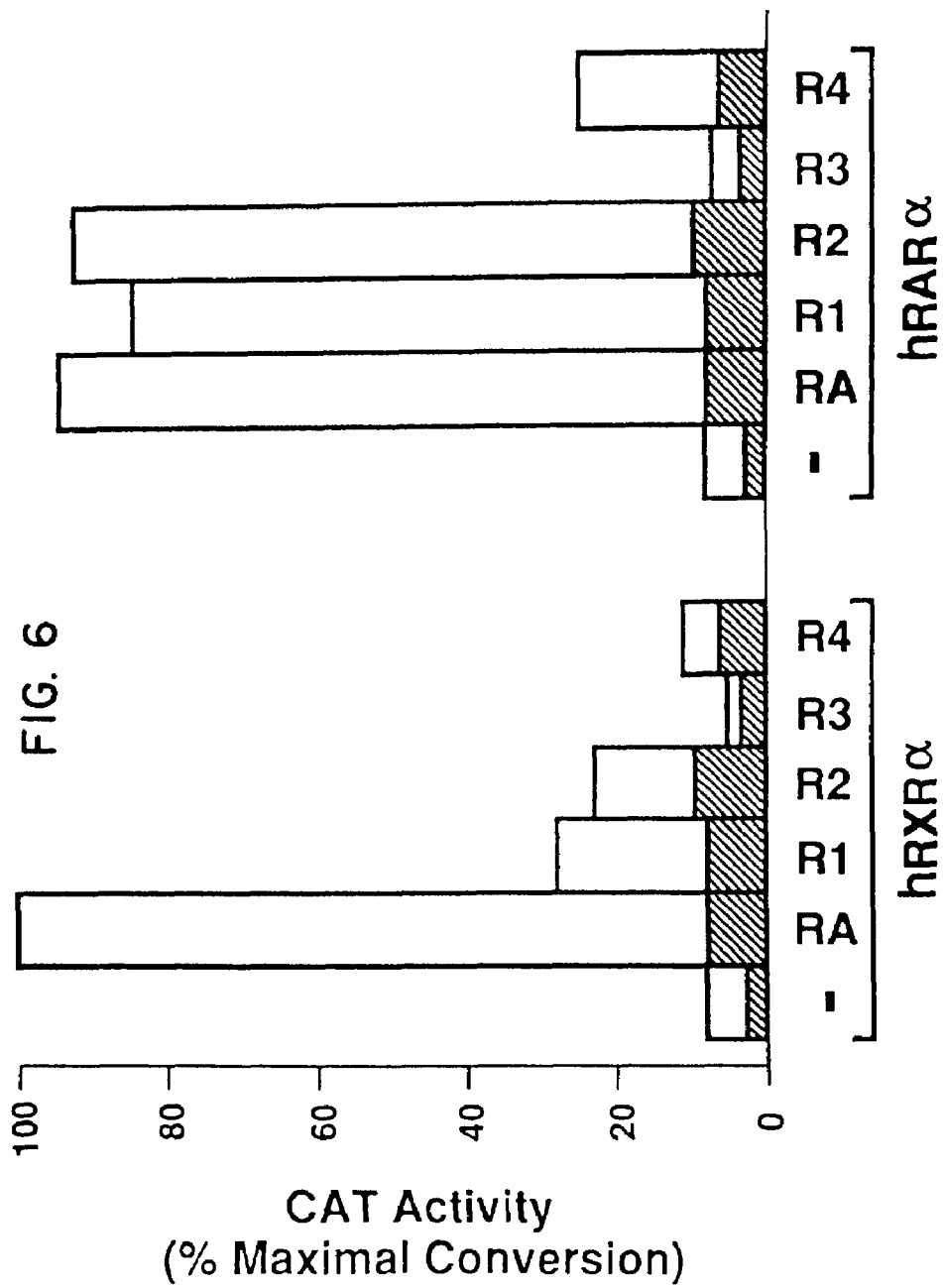
FIG. 6, like FIG. 5, illustrates the differences in transcription-activating activities of hRXR-alpha and hRAR-alpha in mammalian cells in culture containing retinoic acid or different synthetic retinoids.

In FIG. 6, the results are provided for experiments carried out as described in the previous paragraph but with, in place of RAL, RAC, ROH and RP, the synthetic retinoids 4-(5,6,7, 8-tetrahydro-5,5,8,8-tetramethyl-4-iodo-2-antrhracenyl)-benzoic acid ("R1"), ethyl-P-[(E)-2-(5,6,7,8-tetrahydro-5,5, 8,8-tetramethyl-2-naphthyl)-1-propenyl]-benzoic acid ("R2"), ethyl-all trans-9-(4-methoxy-2,3,6-trimethyl)-3,7-dimethyl-2,4,6,8-nonatetranoate ("R3"), and ethyl-all trans-9-(4-methoxy-2,3,6-trimethyl)-3,7-dimethyl-2,4,6,8-nonatetraenoic acid ("R4") initially at a concentration of $10^{-6}$ M. The Figure illustrates production of CAT from the reporter plasmid (delta-MTV-TREp-CAT), CV-1 cells, which are co-transformed with hRXR-alpha-producing expression vector RS-hRXR-alpha or the constitutive hRAR-alpha-producing expression vector RS-hRAR. Experiments are carried out in a medium to which RA, R1, R2, R3, or R4 has been added to a concentration of $10^{-6}$ M. The bars over the "−" sign indicate the levels of CAT production when the cells are exposed to no retinoid. The hatched bars indicate the level of CAT production when a control expression vector, from which no receptor is expressed, is employed in place of the receptor expression vector. The open bars indicate the level of CAT production when receptor-producing expression vector is employed.

Figure 7:
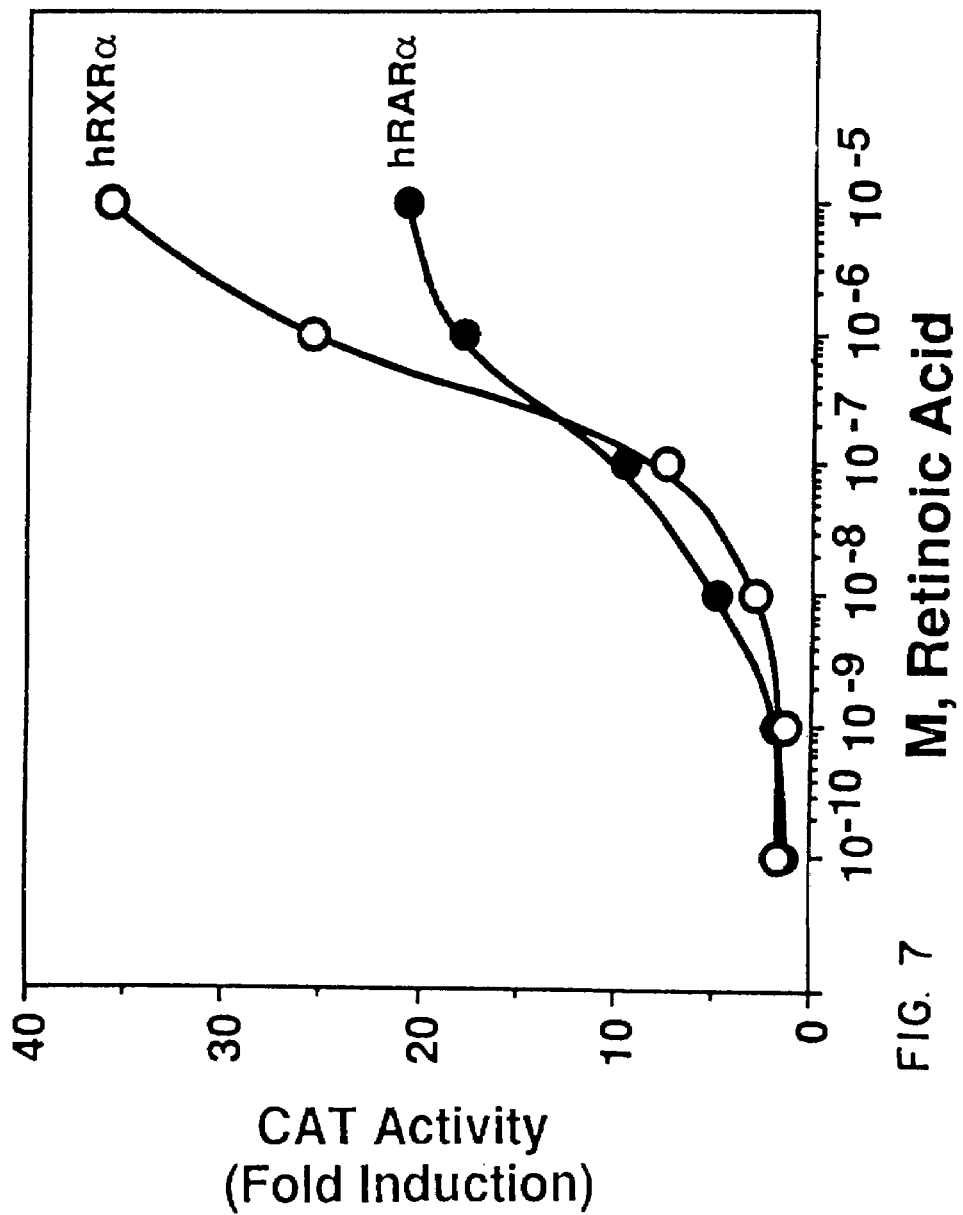
FIG. 7 illustrates the differences between hRXR-alpha and hRAR-alpha in dose-response to retinoic acid in media bathing mammalian cells in which the receptors occur.

In FIG. 7, results are presented for experiments carried out as described in this Example using various concentrations of retinoic acid. The Figure illustrates production of CAT from the reporter plasmid (delta-MTV-TRE$_p$-CAT), in CV-1 cells, which are co-transformed with the receptor-producing expression vector RS-RXR-alpha or RS-RAR-alpha. Experiments are carried out in a medium to which RA has been added to various concentrations. In the Figure, the results are in terms of fold-induction observed with cells exposed to RA, and control cells (exposed to only RA-free ethanol).

Figure 8:
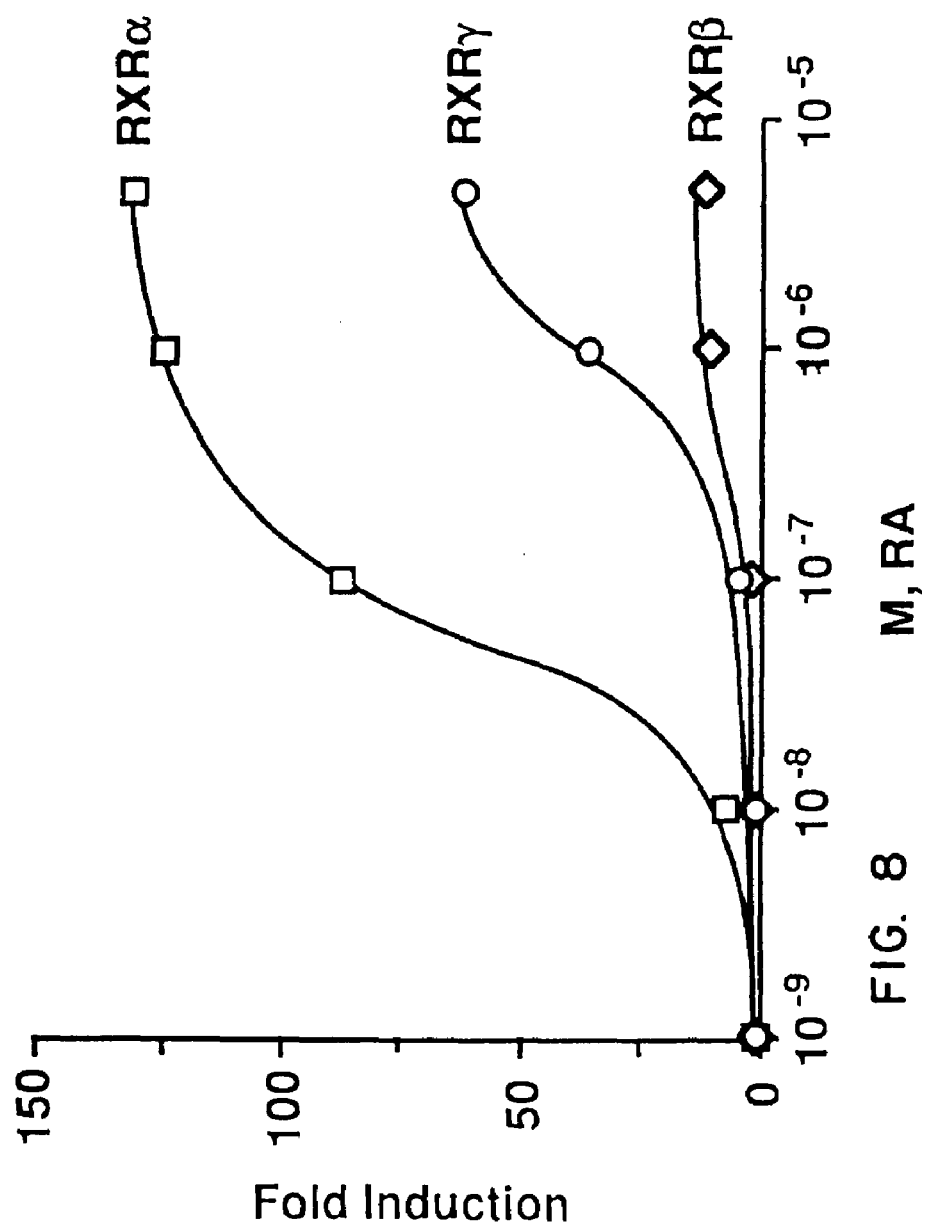
FIG. 8 illustrates the differences between mouse RXR-alpha (mRXRα), mouse RXR-beta (mRXRβ) and mouse RXR-gamma (mRXRγ) in dose response to retinoic acid (RA) in media bathing mammalian cells expressing such receptors.

In FIG. 8, results are presented for experiments carried out as described above, using various concentrations of retinoic acid with expression vectors encoding mRXR-alpha, mRXR-beta and mRXR-gamma.

Figure 9:
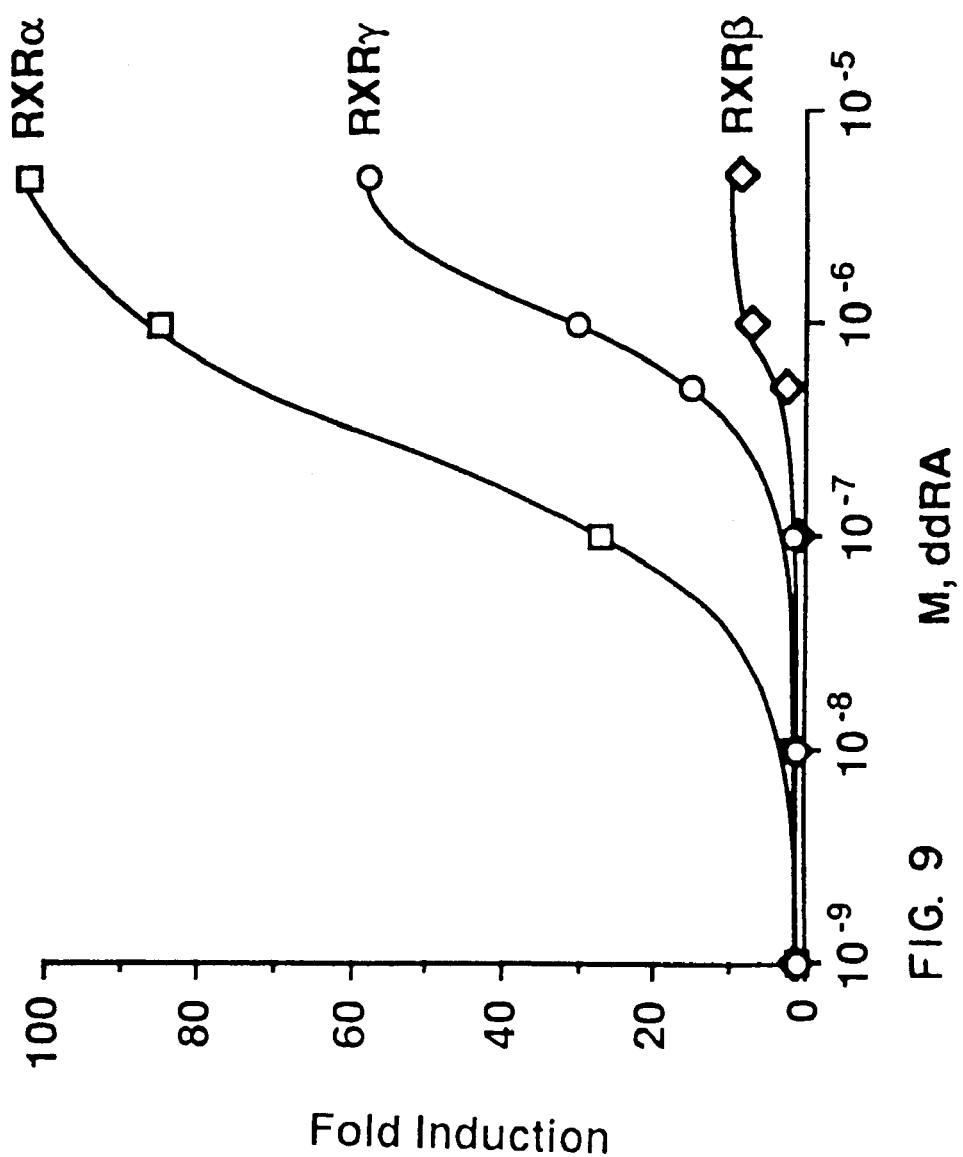
FIG. 9 illustrates the differences between mRXRα, mRXRβ and mRXRγ in dose response to 3,4-didehydroretinoic acid (ddRA) in media bathing mammalian cells expressing such receptors.

In FIG. 9, results are presented for experiments carried out as described above, using various concentrations of 3,4-didehydroretinoic acid (ddRA) with expression vectors encoding mRXR-alpha, mRXR-beta and mRXR-gamma.

Example V

To determine the distribution of hRXR-alpha gene expression, poly A$^+$ RNAs isolated from a variety of adult rat tissues were size fractionated, transferred to a nylon filter, and hybridized with hRXR-alpha cDNA.

Thus, for each tissue of adult male rat that was analyzed, total RNA was prepared from the tissue (see Chomczynski and Sacchi, Anal. Biochem. 162, 156 (1987)) and poly A$^+$ selected by oligo(dT)-cellulose chromatography. Ten micrograms of poly A$^+$ RNA were separated by 1% agarose-ormaldehyde gel electrophoresis, transferred to a Nytran filter (Schleicher and Schuell) (see McDonnell et al., Science 235, 1214 (1987)), and hybridized under stringent conditions with the hRXR-alpha-encoding, EcoRI insert of lambda-XR3-1.

Hybridization was performed at 42° C. in a buffer containing 50% formamide, 5× Denhardt's, 5×SSPE, 0.1% SDS, 100 mg/ml salmon sperm DNA, 200 mg/ml yeast RNA, and [$^{32}$P]-labelled probe. The filter was then washed twice with 2×SSC, 0.1% SDS at 22° C. and twice at 50° C. Autoradiography was for 24h at −70° C. with an intensifying screen. RNA ladder size markers from Bethesda Research Laboratories (Gaithersburg, Md., USA)

The distribution of RXR-alpha mRNA in the rat reveals a pattern of expression distinct from that of the retinoic acid receptors (Giguere et al., Nature 330, 624 (1987); Zelent et al., Nature 339, 714 (1989); Benbrook, Nature 333, 669 (1988)). The rat RXR-alpha message appears to be a single species of about 4.8 kbp (kilobase pairs) which is expressed in many tissues, but most abundantly in the liver, muscle, lung, and kidney and somewhat less abundantly in adrenal, heart, intestine, and spleen.

Example VI

Molecular cloning analyses of the thyroid hormone and retinoic acid receptor genes indicate that each of these receptors belongs to a discreet gene subfamily which encode several receptor isoforms. To determine if this was also true of RXR, a series of Southern blot analyses were carried out. High stringency hybridization of restriction endonuclease-digested human DNA with a labelled DNA fragment derived from lambda-XR3-1 produced a similar number of bands in every digestion, consistent with a single genetic locus. When the hybridization conditions were relaxed, however, many additional bands were observed in the products of each enzyme digestion. Careful inspection of this hybridization pattern demonstrated that it is unrelated to a similar analysis described for hRAR-alpha (Giguere et al., Nature 330, 624 (1987). These observations indicate the presence of at least one other locus in the human genome related to the hRXR-alpha gene. Further, a genomic DNA zooblot representing mammalian, avian, yeast, and *Drosophila* species was obtained. Thus far, the RXR gene family appears to be present in all species tested except yeast, which to date has not been shown to contain any members of the steroid receptor superfamily.

For the analyses of human DNA, two human placenta genomic DNA Southern blots were prepared in parallel with identical DNA samples. The blots were hybridized at high or low stringency with a ⁻1200 bp [$^{32}$P]-labelled fragment of lambda-XR3-1 which included the coding portions of the DNA and ligand binding domains (Sequence ID No. 1, nucleotides 459-1631).

For the zooblot, genomic DNA from human, monkey, rat, mouse, dog, cow, rabbit, chicken, *S. cerevisiae* and *Drosophila melanogaster* were hybridized at low stringency with a ⁻330 bp [$^{32}$P]-labelled fragment of lambda-XR3-1 which included the DNA-binding domain (Sequence ID No. 1, nucleotides 459-776). Differently sized bands (in comparison with HindIII-digested lambda DNA for sizing) were found for the various species. The blots for all of the species (including both for *D. melanogaster*), except yeast, mouse and rabbit appeared to have more than one band.

For the analysis of human DNA, the placental DNA was restricted with BamHI, BglII, EcoRI, HindIII, PstI and PvuII, separated in a 0.8% agarose gel (10 μg per lane) and transferred to nitrocellulose (see McDonnell et al., supra) and hybridized as described below.

For the zooblot, EcoRI-digested DNA from the several species (Clontech, Palo Alto, Calif., USA), other than *D. melanogaster*, was used for Southern blot analysis. EcoRI- and XhoI-digested *D. melanogaster* DNA was included also.

Blots were hybridized at 42° C. in the low stringency buffer described in Example I or at high stringency in the same buffer modified by addition of formamide to 50%. Low stringency blots were washed twice at room temperature and twice at 50° C. in 2>: SSC, 0.1. SDS. The high stringency blot was washed twice at room temperature in 2×SSC, 0.1% SDS and twice at 65° C. in 0.5×SSC, 0.1% SDS.

Example VII

Northern analysis were carried out on the mouse RXR isoforms alpha, beta and gamma, to determine the tissue distribution of these receptors in adult tissues and in developing embryos.

Thus, mRNA (10 μg) was isolated from various adult rat tissues of from day 10.5-day 18.5 p.c. whole mouse embryos. These samples were subjected to Northern analysis using $^{32}$P-labeled cDNA probes derived from regions specific to mRXRβ, mRXRβ, or mRXRγ.

In the adult, the various RXR isoforms are seen to be expressed in both a specific and overlapping distribution pattern.

In the embryo, the various isoforms are highly expressed in what appears to be a specific temporal pattern.

The invention has been described in detail with particular reference to preferred embodiments thereof, but it will be understood that variations and modifications can be effected within the spirit and scope of the invention.

Figure 2:
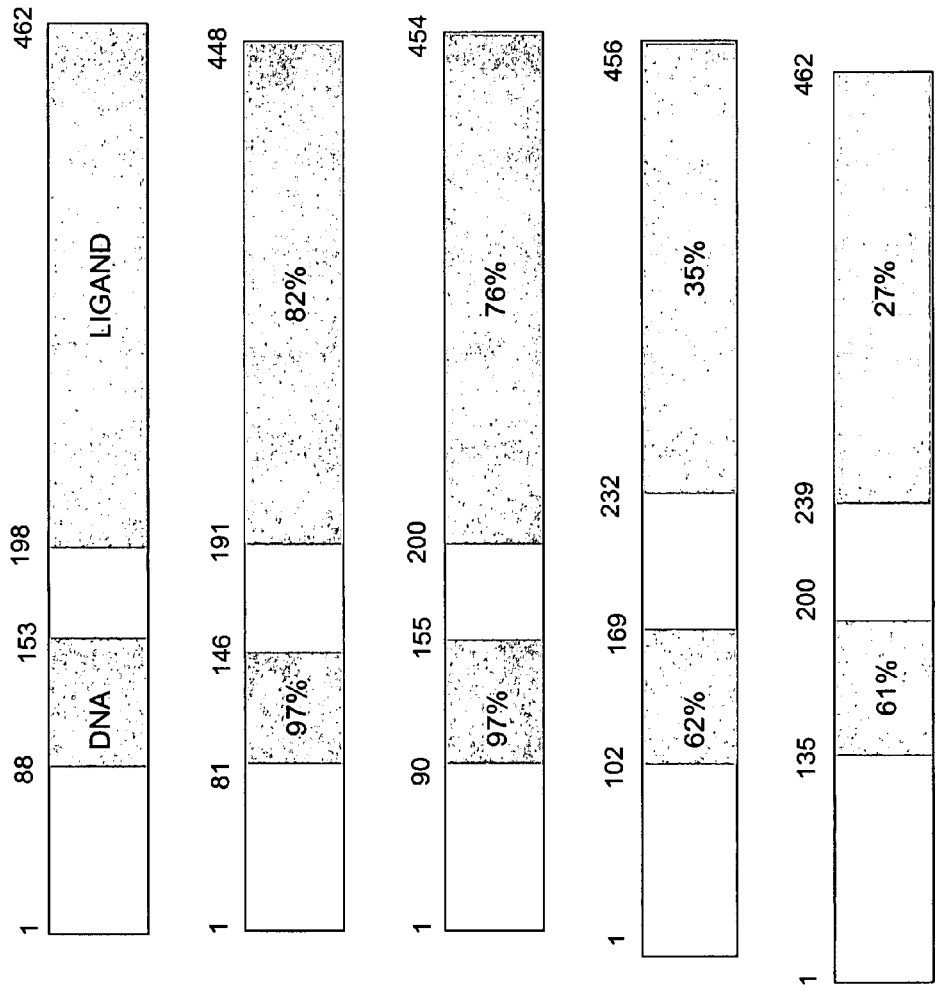
FIG. 2 shows the extent of amino acid identity (i.e., "homology") between the DNA binding domain ("DNA") and ligand binding domain ("LIGAND") of human RAR alpha (hRARα), relative to the corresponding domains of human retinoic acid receptor-beta (hRARβ), human retinoic acid receptor-gamma (hRARγ), hTRβ and hRXRα.

Deposit on Jan. 31, 1990, a sample of replicatable phagescript SK double-stranded DNA (Stratagene, La Jolla, Calif., USA), with the 1860 base-pair, EcoRI-site-bounded DNA, the sequence of which is illustrated in FIG. 1, inserted at the unique EcoRI site, was deposited under the terms of the Budapest Treaty on the International Recognition of the Deposit of Microorganisms for the Purposes of Patent Procedure at the American Type Culture Collection, Rockville, Md., USA ("ATCC"). The accession number assigned to this deposit is ATCC 40741. The deposited DNA is designated pSK(hRXR-alpha).

Phagescript SK double-stranded DNA is a modified M13mp18 bacteriophage DNA (double-stranded). Derivatives, such as pSK(hRXR-alpha), of phagescript SK double-stranded DNA can be cloned in the same way as M13mp18 and its derivatives.

Samples of pSK(hRXR-alpha) will be publicly available from the ATCC without restriction, except as provided in 37 CFR 1.801 et seq., at the latest on the date an United States Patent first issues on this application or a continuing application thereof. Otherwise, in accordance with the Budapest Treaty and the regulations promulgated thereunder, samples will be available from the ATCC to all persons legally entitled to receive them under the law and regulations of any country or international organization in which an application, claiming priority of this application, is filed or in which a patent based on any such application is granted.

SUMMARY OF SEQUENCES

Sequence ID No. 1 is the coding sequence of an EcoRI-site-bounded DNA segment which encodes the novel receptor disclosed herein, referred to as human RXR-alpha [hRXRα].

Sequence ID No. 2 is the amino acid sequence of the novel receptor referred to herein as hRXRα.

Sequence ID No. 3 is the nucleotide (and amino acid) sequence of the novel receptor disclosed herein, referred to as mouse RXR-alpha [mRXRα].

Sequence ID No. 4 is the amino acid sequence of the novel receptor referred to herein as mRXRα.

Sequence ID No. 5 is the nucleotide (and amino acid) sequence of the novel receptor disclosed herein, referred to as mouse RXR-gamma [mRXRγ].

Sequence ID No. 6 is the amino acid sequence of the novel receptor referred to herein as mRXRγ.

Sequence ID No. 7 is the nucleotide sequence of the receptor disclosed by Hamada, et al in PNAS 86: 8298-8293 (1989). This receptor is similar to the receptor referred to herein as mRXRβ.

Sequence ID No. 8 is the amino acid sequence of the receptor disclosed by Hamada, et al in PNAS 86: 8298-8293 (1989).

Sequence ID No. 9 is the nucleotide linker used in the formation of A5C-RXR-alpha.

Sequence ID No. 10 is the palindromic thyroid hormone response element TREp of ADH-TREp-CAT.

Sequence ID No. 11 is one strand of the oligonucleotide used in the formation of ADH-TREp-CAT.

Sequence ID No. 12 is the second strand of the oligonucleotide used in the formation of ADH-TREp-CAT, which is complementary to Sequence ID No. 11.

The invention claimed is:

1. A purified retinoid receptor characterized by:
   (1) being responsive to the presence of retinoid ligand(s) to regulate the transcription of associated gene(s);
   (2) being a member of the steroid/thyroid hormone superfamily of receptors having an N-terminal domain, a DNA binding domain and a C-terminal domain, wherein:
      (i) said N-terminal domain has at least 36% amino acid identity with amino acid residues 1-140 of Sequence ID No. 4; and
      (ii) said DNA binding domain has about 66 amino acids with 9 Cys residues, and has:
         (a) at least 92% amino acid identity with the DNA binding domain of mRXR-alpha defined by residues 140-205 of Sequence ID No. 4,
         (b) less than about 65% amino acid identity with the DNA binding domain of hRAR-alpha,
         (c) less than about 55% amino acid identity with the DNA binding domain of hTR-beta, and
         (d) less than about 55% amino acid identity with the DNA binding domain of hGR;
   (3) not including the amino acid sequence set forth in Sequence ID No. 8.

2. A receptor according to claim 1 wherein said receptor comprises the same sequence as that of:
   amino acids 1-462 shown in Sequence ID No. 2 (hRXR-α),
   amino acids 1-467 shown in Sequence in Sequence ID No. 4 (mRXR-α), or
   amino acids 1-463 shown in Sequence ID No. 6 (mRXR-γ).

3. A receptor according to claim 1 wherein said receptor comprises a DNA binding domain with the same sequence as that of:
   amino acids 135-200 shown in Sequence ID No. 2 (hRXR-α),
   amino acids 140-205 shown in Sequence ID No. 4 (mRXR-α), or
   amino acids 139-204 shown in Sequence ID No. 6 (mRXR-γ).

4. A receptor according to claim 1 which comprises a segment encoded by a continuous nucleotide sequence which is substantially the same as:
   nucleotides 76-1464 shown in Sequence ID No. 1 encoding amino acids 1-462 shown in Sequence ID No. 2 (hRXR-α),
   nucleotides 181-1581 shown in Sequence ID No. 3 encoding amino acids 1-467 shown in Sequence in Sequence ID No. 4-α), or
   nucleotides 123-1514 shown in Sequence ID No. 5 encoding amino acids 1-463 shown in Sequence ID No. 6 (mRXR-γ).

5. A receptor according to claim 4, wherein said receptor is encoded by plastid pSK (hRXR-alpha) (ATCC 40741).

6. A receptor according to claim 1 wherein the nucleic acid encoding said retinoid receptor is operatively associated with the *Drosophila* actin 5C promoter (A5C) or the 5'-LTR promoter of the rous sarcoma virus proviral DNA for expression of said retinoid receptor.

* * * * *

SEQUENCE LISTING

```
<160> NUMBER OF SEQ ID NOS: 12

<210> SEQ ID NO 1
<211> LENGTH: 1866
<212> TYPE: DNA
<213> ORGANISM: Homo sapiens
<220> FEATURE:
<221> NAME/KEY: CDS
<222> LOCATION: (76)..(1461)

<400> SEQUENCE: 1
gaattccggc gccgggggcc gcccgcccgc cgcccgctgc ctgcgccgcc ggccgggcat      60
gagttagtcg cagac atg gac acc aaa cat ttc ctg ccg ctc gat ttc tcc     111
                Met Asp Thr Lys His Phe Leu Pro Leu Asp Phe Ser
                  1               5                  10 acc cag gtg aac tcc tcc ctc acc tcc ccg acg ggg cga ggc tcc atg     159
Thr Gln Val Asn Ser Ser Leu Thr Ser Pro Thr Gly Arg Gly Ser Met
             15                  20                  25 gct gcc ccc tcg ctg cac ccg tcc ctg ggg cct ggc atc ggc tcc ccg     207
Ala Ala Pro Ser Leu His Pro Ser Leu Gly Pro Gly Ile Gly Ser Pro
         30                  35                  40 gga cag ctg cat tct ccc atc agc acc ctg agc tcc ccc atc aac ggc     255
Gly Gln Leu His Ser Pro Ile Ser Thr Leu Ser Ser Pro Ile Asn Gly
 45                  50                  55                  60 atg ggc ccg cct ttc tcg gtc atc agc tcc ccc atg ggc ccc cac tcc     303
Met Gly Pro Pro Phe Ser Val Ile Ser Ser Pro Met Gly Pro His Ser
                 65                  70                  75 atg tcg gtg ccc acc aca ccc acc ctg ggc ttc agc act ggc agc ccc     351
Met Ser Val Pro Thr Thr Pro Thr Leu Gly Phe Ser Thr Gly Ser Pro
             80                  85                  90 cag ctc agc tca cct atg aac ccc gtc agc agc agc gag gac atc aag     399
Gln Leu Ser Ser Pro Met Asn Pro Val Ser Ser Ser Glu Asp Ile Lys
         95                 100                 105 ccc ccc ctg ggc ctc aat ggc gtc ctc aag gtc ccc gcc cac ccc tca     447
Pro Pro Leu Gly Leu Asn Gly Val Leu Lys Val Pro Ala His Pro Ser
110                 115                 120 gga aac atg gct tcc ttc acc aag cac atc tgc gcc atc tgc ggg gac     495
Gly Asn Met Ala Ser Phe Thr Lys His Ile Cys Ala Ile Cys Gly Asp
125                 130                 135                 140 cgc tcc tca ggc aag cac tat gga gtg tac agc tgc gag ggg tgc aag     543
Arg Ser Ser Gly Lys His Tyr Gly Val Tyr Ser Cys Glu Gly Cys Lys
                145                 150                 155 ggc ttc ttc aag cgg acg gtg cgc aag gac ctg acc tac acc tgc cgc     591
Gly Phe Phe Lys Arg Thr Val Arg Lys Asp Leu Thr Tyr Thr Cys Arg
            160                 165                 170 gac aac aag gac tgc ctg att gac aag cgg cag cgg aac cgg tgc cag     639
Asp Asn Lys Asp Cys Leu Ile Asp Lys Arg Gln Arg Asn Arg Cys Gln
```

```
                    175                 180                 185
tac tgc cgc tac cag aag tgc ctg gcc atg ggc atg aag cgg gaa gcc      687
Tyr Cys Arg Tyr Gln Lys Cys Leu Ala Met Gly Met Lys Arg Glu Ala
    190                 195                 200 gtg cag gag gag cgg cag cgt ggc aag gac cgg aac gag aat gag gtg      735
Val Gln Glu Glu Arg Gln Arg Gly Lys Asp Arg Asn Glu Asn Glu Val
205                 210                 215                 220 gag tcg acc agc agc gcc aac gag gac atg ccg gtg gag agg atc ctg      783
Glu Ser Thr Ser Ser Ala Asn Glu Asp Met Pro Val Glu Arg Ile Leu
                225                 230                 235 gag gct gag ctg gcc gtg gag ccc aag acc gag acc tac gtg gag gca      831
Glu Ala Glu Leu Ala Val Glu Pro Lys Thr Glu Thr Tyr Val Glu Ala
            240                 245                 250 aac atg ggg ctg aac ccc agc tcg ccg aac gac cct gtc acc aac att      879
Asn Met Gly Leu Asn Pro Ser Ser Pro Asn Asp Pro Val Thr Asn Ile
        255                 260                 265 tgc caa gca gcc gac aaa cag ctt ttc acc ctg gtg gag tgg gcc aag      927
Cys Gln Ala Ala Asp Lys Gln Leu Phe Thr Leu Val Glu Trp Ala Lys
    270                 275                 280 cgg atc cca cac ttc tca gag ctg ccc ctg gac gac cag gtc atc ctg      975
Arg Ile Pro His Phe Ser Glu Leu Pro Leu Asp Asp Gln Val Ile Leu
285                 290                 295                 300 ctg cgg gca ggc tgg aat gag ctg ctc atc gcc tcc ttc tcc cac cgc     1023
Leu Arg Ala Gly Trp Asn Glu Leu Leu Ile Ala Ser Phe Ser His Arg
                305                 310                 315 tcc atc gcc gtg aag gac ggg atc ctc ctg gcc acc ggg ctg cac gtc     1071
Ser Ile Ala Val Lys Asp Gly Ile Leu Leu Ala Thr Gly Leu His Val
            320                 325                 330 cac cgg aac agc gcc cac agc gca ggg gtg ggc gcc atc ttt gac agg     1119
His Arg Asn Ser Ala His Ser Ala Gly Val Gly Ala Ile Phe Asp Arg
        335                 340                 345 gtg ctg acg gag ctt gtg tcc aag atg cgg gac atg cag atg gac aag     1167
Val Leu Thr Glu Leu Val Ser Lys Met Arg Asp Met Gln Met Asp Lys
    350                 355                 360 acg gag ctg ggc tgc ctg cgc gcc atc gtc ctc ttt aac cct gac tcc     1215
Thr Glu Leu Gly Cys Leu Arg Ala Ile Val Leu Phe Asn Pro Asp Ser
365                 370                 375                 380 aag ggg ctc tcg aac ccg gcc gag gtg gag gcg ctg agg gag aag gtc     1263
Lys Gly Leu Ser Asn Pro Ala Glu Val Glu Ala Leu Arg Glu Lys Val
                385                 390                 395 tat gcg tcc ttg gag gcc tac tgc aag cac aag tac cca gag cag ccg     1311
Tyr Ala Ser Leu Glu Ala Tyr Cys Lys His Lys Tyr Pro Glu Gln Pro
            400                 405                 410 gga agg ttc gct aag ctc ttg ctc cgc ctg ccg gct ctg cgc tcc atc     1359
Gly Arg Phe Ala Lys Leu Leu Leu Arg Leu Pro Ala Leu Arg Ser Ile
        415                 420                 425 ggg ctc aaa tgc ctg gaa cat ctc ttc ttc ttc aag ctc atc ggg gac     1407
Gly Leu Lys Cys Leu Glu His Leu Phe Phe Phe Lys Leu Ile Gly Asp
    430                 435                 440 aca ccc att gac acc ttc ctt atg gag atg ctg gag gcg ccg cac caa     1455
Thr Pro Ile Asp Thr Phe Leu Met Glu Met Leu Glu Ala Pro His Gln
445                 450                 455                 460 atg act taggcctgcg ggcccatcct tgtgcccac ccgttctggc cacccctgcct       1511
Met Thr ggacgccagc tgttcttctc agcctgagcc ctgtccctgc ccttctctgc ctggcctgtt    1571
tggactttgg ggcacagcct gtcactgctc tgcctaagag atgtgttgtc accctcctta    1631
tttctgttac tacttgtctg tggcccaggg cagtggcttt cctgagcagc agccttcgtg    1691
```

-continued

```
gcaagaacta gcgtgagccc agccaggcgc ctccccaccg ggctctcagg acgccctgcc   1751
acacccacgg ggcttgggcg actacagggt cttcggcccc agccctggag ctgcaggagt   1811
tgggaacggg gcttttgttt ccgttgctgt ttatcgatgc tggttttcag aattc        1866
```

<210> SEQ ID NO 2
<211> LENGTH: 462
<212> TYPE: PRT
<213> ORGANISM: Homo sapiens

<400> SEQUENCE: 2

```
Met Asp Thr Lys His Phe Leu Pro Leu Asp Phe Ser Thr Gln Val Asn
  1               5                  10                  15

Ser Ser Leu Thr Ser Pro Thr Gly Arg Gly Ser Met Ala Ala Pro Ser
                 20                  25                  30

Leu His Pro Ser Leu Gly Pro Gly Ile Gly Ser Pro Gly Gln Leu His
             35                  40                  45

Ser Pro Ile Ser Thr Leu Ser Ser Pro Ile Asn Gly Met Gly Pro Pro
         50                  55                  60

Phe Ser Val Ile Ser Ser Pro Met Gly Pro His Ser Met Ser Val Pro
 65                  70                  75                  80

Thr Thr Pro Thr Leu Gly Phe Ser Thr Gly Ser Pro Gln Leu Ser Ser
                 85                  90                  95

Pro Met Asn Pro Val Ser Ser Glu Asp Ile Lys Pro Pro Leu Gly Leu
            100                 105                 110

Leu Asn Gly Val Leu Lys Val Pro Ala His Pro Ser Gly Asn Met Ala
        115                 120                 125

Ser Phe Thr Lys His Ile Cys Ala Ile Cys Gly Asp Arg Ser Ser Gly
    130                 135                 140

Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
            180                 185                 190

Gln Lys Cys Leu Ala Met Gly Met Lys Arg Glu Ala Val Gln Glu Glu
        195                 200                 205

Arg Gln Arg Gly Lys Asp Arg Asn Glu Asn Glu Val Glu Ser Thr Ser
    210                 215                 220

Ser Ala Asn Glu Asp Met Pro Val Glu Arg Ile Leu Glu Ala Glu Leu
225                 230                 235                 240

Ala Val Glu Pro Lys Thr Glu Thr Tyr Val Glu Ala Asn Met Gly Leu
                245                 250                 255

Asn Pro Ser Ser Pro Asn Asp Pro Val Thr Asn Ile Cys Gln Ala Ala
            260                 265                 270

Asp Lys Gln Leu Phe Thr Leu Val Glu Trp Ala Lys Arg Ile Pro His
        275                 280                 285

Phe Ser Glu Leu Pro Leu Asp Asp Gln Val Ile Leu Leu Arg Ala Gly
    290                 295                 300

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
                325                 330                 335

Ala His Ser Ala Gly Val Gly Ala Ile Phe Asp Arg Val Leu Thr Glu
            340                 345                 350
```

-continued

```
Leu Val Ser Lys Met Arg Asp Met Gln Met Asp Lys Thr Glu Leu Gly
            355                 360                 365

Cys Leu Arg Ala Ile Val Leu Phe Asn Pro Asp Ser Lys Gly Leu Ser
            370                 375                 380

Asn Pro Ala Glu Val Glu Ala Leu Arg Glu Lys Val Tyr Ala Ser Leu
385                 390                 395                 400

Glu Ala Tyr Cys Lys His Lys Tyr Pro Glu Gln Pro Gly Arg Phe Ala
                405                 410                 415

Lys Leu Leu Leu Arg Leu Pro Ala Leu Arg Ser Ile Gly Leu Lys Cys
                420                 425                 430

Leu Glu His Leu Phe Phe Lys Leu Ile Gly Asp Thr Pro Ile Asp
            435                 440                 445

Thr Phe Leu Met Glu Met Leu Glu Ala Pro His Gln Met Thr
    450                 455                 460

<210> SEQ ID NO 3
<211> LENGTH: 2095
<212> TYPE: DNA
<213> ORGANISM: Mus sp.
<220> FEATURE:
<221> NAME/KEY: CDS
<222> LOCATION: (178)..(1578)

<400> SEQUENCE: 3
gaattcgcgg ccgcggcgac ttttgcaaca actcgccgcg ccgcggcctc cgcgcgccgc    60
cgccgccgct gccgccgccg gctccccgcc gcccgggccc cgggcgggcc gcgcggggg   120 ccgccgcgct gccgccctgc tgctccgccg ccggctgggc atgagttagt cgcagac    177 atg gac acc aaa cat ttc ctg ccg ctc gac ttc tct acc cag gtg aac   225
Met Asp Thr Lys His Phe Leu Pro Leu Asp Phe Ser Thr Gln Val Asn
  1               5                  10                  15 tct tcg tcc ctc aac tct cca acg ggt cga ggc tcc atg gct gtc ccc   273
Ser Ser Ser Leu Asn Ser Pro Thr Gly Arg Gly Ser Met Ala Val Pro
                 20                  25                  30 tcg ctg cac ccc tcc ttg ggt ccg gga atc ggc tct cca ctg ggc tcg   321
Ser Leu His Pro Ser Leu Gly Pro Gly Ile Gly Ser Pro Leu Gly Ser
             35                  40                  45 cct ggg cag ctg cac tct cct atc agc acc ctg agc tcc ccc atc aat   369
Pro Gly Gln Leu His Ser Pro Ile Ser Thr Leu Ser Ser Pro Ile Asn
         50                  55                  60 ggc atg ggt ccg ccc ttc tct gtc atc agc tcc ccc atg ggc ccg cac   417
Gly Met Gly Pro Pro Phe Ser Val Ile Ser Ser Pro Met Gly Pro His
 65                  70                  75                  80 tcc atg tcg gta ccc acc aca ccc aca ttg ggc ttc ggg act ggt agc   465
Ser Met Ser Val Pro Thr Thr Pro Thr Leu Gly Phe Gly Thr Gly Ser
                 85                  90                  95 ccc cag ctc aat tca ccc atg aac cct gtg agc agc act gag gat atc   513
Pro Gln Leu Asn Ser Pro Met Asn Pro Val Ser Ser Thr Glu Asp Ile
            100                 105                 110 aag ccg cca cta ggc ctc aat ggc gtc ctc aag gtt cct gcc cat ccc   561
Lys Pro Pro Leu Gly Leu Asn Gly Val Leu Lys Val Pro Ala His Pro
        115                 120                 125 tca gga aat atg gcc tcc ttc acc aag cac atc tgt gct atc tgt ggg   609
Ser Gly Asn Met Ala Ser Phe Thr Lys His Ile Cys Ala Ile Cys Gly
    130                 135                 140 gac cgc tcc tca ggc aaa cac tat ggg gta tac agt tgt gag ggc tgc   657
Asp Arg Ser Ser Gly Lys His Tyr Gly Val Tyr Ser Cys Glu Gly Cys
145                 150                 155                 160
```

```
aag ggc ttc ttc aag agg aca gta cgc aaa gac ctg acc tac acc tgc      705
Lys Gly Phe Phe Lys Arg Thr Val Arg Lys Asp Leu Thr Tyr Thr Cys
                165                 170                 175 cga gac aac aag gac tgc ctg atc gac aag aga cag cgg aac cgg tgt      753
Arg Asp Asn Lys Asp Cys Leu Ile Asp Lys Arg Gln Arg Asn Arg Cys
                180                 185                 190 cag tac tgc cgc tac cag aag tgc ctg gcc atg ggc atg aag cgg gaa      801
Gln Tyr Cys Arg Tyr Gln Lys Cys Leu Ala Met Gly Met Lys Arg Glu
                195                 200                 205 gct gtg cag gag gag cgg cag cgg ggc aag gac cgg aat gag aac gag      849
Ala Val Gln Glu Glu Arg Gln Arg Gly Lys Asp Arg Asn Glu Asn Glu
        210                 215                 220 gtg gag tcc acc agc agt gcc aac gag gac atg cct gta gag aag att      897
Val Glu Ser Thr Ser Ser Ala Asn Glu Asp Met Pro Val Glu Lys Ile
225                 230                 235                 240 ctg gaa gcc gag ctt gct gtc gag ccc aag act gag aca tac gtg gag      945
Leu Glu Ala Glu Leu Ala Val Glu Pro Lys Thr Glu Thr Tyr Val Glu
                245                 250                 255 gca aac atg ggg ctg aac ccc agc tca cca aat gac cct gtt acc aac      993
Ala Asn Met Gly Leu Asn Pro Ser Ser Pro Asn Asp Pro Val Thr Asn
                260                 265                 270 atc tgt caa gca gca gac aag cag ctc ttc act ctt gtg gag tgg gcc     1041
Ile Cys Gln Ala Ala Asp Lys Gln Leu Phe Thr Leu Val Glu Trp Ala
                275                 280                 285 aag agg atc cca cac ttt tct gag ctg ccc cta gac gac cag gtc atc     1089
Lys Arg Ile Pro His Phe Ser Glu Leu Pro Leu Asp Asp Gln Val Ile
        290                 295                 300 ctg cta cgg gca ggc tgg aac gag ctg ctg atc gcc tcc ttc tcc cac     1137
Leu Leu Arg Ala Gly Trp Asn Glu Leu Leu Ile Ala Ser Phe Ser His
305                 310                 315                 320 cgc tcc ata gct gtg aaa gat ggg att ctc ctg gcc acc ggg ctg cac     1185
Arg Ser Ile Ala Val Lys Asp Gly Ile Leu Leu Ala Thr Gly Leu His
                325                 330                 335 gta cac cgg aac agc gct cac agt gct ggg gtg ggc gcc atc ttt gac     1233
Val His Arg Asn Ser Ala His Ser Ala Gly Val Gly Ala Ile Phe Asp
                340                 345                 350 agg gtg cta aca gag ctg gtg tct aag atg cgt gac atg cag atg gac     1281
Arg Val Leu Thr Glu Leu Val Ser Lys Met Arg Asp Met Gln Met Asp
        355                 360                 365 aag acg gag ctg ggc tgc ctg cga gcc att gtc ctg ttc aac cct gac     1329
Lys Thr Glu Leu Gly Cys Leu Arg Ala Ile Val Leu Phe Asn Pro Asp
        370                 375                 380 tct aag ggg ctc tca aac cct gct gag gtg gag gcg ttg agg gag aag     1377
Ser Lys Gly Leu Ser Asn Pro Ala Glu Val Glu Ala Leu Arg Glu Lys
385                 390                 395                 400 gtg tat gcg tca cta gaa gcg tac tgc aaa cac aag tac cct gag cag     1425
Val Tyr Ala Ser Leu Glu Ala Tyr Cys Lys His Lys Tyr Pro Glu Gln
                405                 410                 415 ccg ggc agg ttt gcc aag ctg ctc ctc cgc ctg cct gca ctg cgt tcc     1473
Pro Gly Arg Phe Ala Lys Leu Leu Leu Arg Leu Pro Ala Leu Arg Ser
                420                 425                 430 atc ggg ctc aag tgc ctg gag cac ctg ttc ttc ttc aag ctc atc ggg     1521
Ile Gly Leu Lys Cys Leu Glu His Leu Phe Phe Phe Lys Leu Ile Gly
                435                 440                 445 gac acg ccc atc gac acc ttc ctc atg gag atg ctg gag gca cca cat     1569
Asp Thr Pro Ile Asp Thr Phe Leu Met Glu Met Leu Glu Ala Pro His
        450                 455                 460 caa gcc acc taggcccccg ccgccgtgtg ccggtcccgt gccctgcctg             1618
Gln Ala Thr
465
```

-continued

```
gacacagctg ctcagctcca gccctgcccc tgcccttcct gatggcccgt gtggatcttt    1678
ggggtgcagt gtccttatgg gcccaaaaga tgcatcacca tcctcgccat ctttactcat    1738
gcttgccttt ggcccagggc atagcagagc tggtgtgaca cctggccagc tcctgcccta    1798
catcaggctc taaggctatg ctgctgtcac cccgagggtc gtggggttcg tcatggggcc    1858
ttcagcacct ggagctgcaa gagctgggaa aagggcttgt tctggttgct ggttgctggt    1918
cgctggttct cgacatccca catggcacct ctgtttggag tgccccatct tggcctgttc    1978
agagtcctgg tacccagtta gggtgggaat ccacctggga tcaagaagga gcaggtgggg    2038
caggccgtat cctcctgggt catagctaac ctataaaggc gccgcgaatt cctcgag      2095
```

<210> SEQ ID NO 4
<211> LENGTH: 467
<212> TYPE: PRT
<213> ORGANISM: Mus sp.

<400> SEQUENCE: 4

```
Met Asp Thr Lys His Phe Leu Pro Leu Asp Phe Ser Thr Gln Val Asn
  1               5                  10                  15

Ser Ser Ser Leu Asn Ser Pro Thr Gly Arg Gly Ser Met Ala Val Pro
                 20                  25                  30

Ser Leu His Pro Ser Leu Gly Pro Gly Ile Gly Ser Pro Leu Gly Ser
             35                  40                  45

Pro Gly Gln Leu His Ser Pro Ile Ser Thr Leu Ser Ser Pro Ile Asn
         50                  55                  60

Gly Met Gly Pro Pro Phe Ser Val Ile Ser Ser Pro Met Gly Pro His
 65                  70                  75                  80

Ser Met Ser Val Pro Thr Thr Pro Thr Leu Gly Phe Gly Thr Gly Ser
                 85                  90                  95

Pro Gln Leu Asn Ser Pro Met Asn Pro Val Ser Ser Thr Glu Asp Ile
                100                 105                 110

Lys Pro Pro Leu Gly Leu Asn Gly Val Leu Lys Val Pro Ala His Pro
            115                 120                 125

Ser Gly Asn Met Ala Ser Phe Thr Lys His Ile Cys Ala Ile Cys Gly
        130                 135                 140

Asp Arg Ser Ser Gly Lys His Tyr Gly Val Tyr Ser Cys Glu Gly Cys
145                 150                 155                 160

Lys Gly Phe Phe Lys Arg Thr Val Arg Lys Asp Leu Thr Tyr Thr Cys
                165                 170                 175

Arg Asp Asn Lys Asp Cys Leu Ile Asp Lys Arg Gln Arg Asn Arg Cys
            180                 185                 190

Gln Tyr Cys Arg Tyr Gln Lys Cys Leu Ala Met Gly Met Lys Arg Glu
        195                 200                 205

Ala Val Gln Glu Glu Arg Gln Arg Gly Lys Asp Arg Asn Glu Asn Glu
    210                 215                 220

Val Glu Ser Thr Ser Ser Ala Asn Glu Asp Met Pro Val Glu Lys Ile
225                 230                 235                 240

Leu Glu Ala Glu Leu Ala Val Glu Pro Lys Thr Glu Thr Tyr Val Glu
                245                 250                 255

Ala Asn Met Gly Leu Asn Pro Ser Ser Pro Asn Asp Pro Val Thr Asn
            260                 265                 270

Ile Cys Gln Ala Ala Asp Lys Gln Leu Phe Thr Leu Val Glu Trp Ala
        275                 280                 285
```

```
Lys Arg Ile Pro His Phe Ser Glu Leu Pro Leu Asp Asp Gln Val Ile
290                 295                 300

Leu Leu Arg Ala Gly Trp Asn Glu Leu Leu Ile Ala Ser Phe Ser His
305                 310                 315                 320

Arg Ser Ile Ala Val Lys Asp Gly Ile Leu Leu Ala Thr Gly Leu His
                325                 330                 335

Val His Arg Asn Ser Ala His Ser Ala Gly Val Gly Ala Ile Phe Asp
                340                 345                 350

Arg Val Leu Thr Glu Leu Val Ser Lys Met Arg Asp Met Gln Met Asp
                355                 360                 365

Lys Thr Glu Leu Gly Cys Leu Arg Ala Ile Val Leu Phe Asn Pro Asp
370                 375                 380

Ser Lys Gly Leu Ser Asn Pro Ala Glu Val Glu Ala Leu Arg Glu Lys
385                 390                 395                 400

Val Tyr Ala Ser Leu Glu Ala Tyr Cys Lys His Lys Tyr Pro Glu Gln
                405                 410                 415

Pro Gly Arg Phe Ala Lys Leu Leu Leu Arg Leu Pro Ala Leu Arg Ser
                420                 425                 430

Ile Gly Leu Lys Cys Leu Glu His Leu Phe Phe Phe Lys Leu Ile Gly
                435                 440                 445

Asp Thr Pro Ile Asp Thr Phe Leu Met Glu Met Leu Glu Ala Pro His
450                 455                 460

Gln Ala Thr
465

<210> SEQ ID NO 5
<211> LENGTH: 1662
<212> TYPE: DNA
<213> ORGANISM: Mus sp.
<220> FEATURE:
<221> NAME/KEY: CDS
<222> LOCATION: (123)..(1511)

<400> SEQUENCE: 5
gaattcgcgg ccgcgctgtg cctgggagcc gagagagaga gagagagaga gagagagaga      60
gagagagaga gagaggctgt actcttcaga agcgcacgag aggaatgaac tgagcagcca     120 ac atg tat gga aat tat tcc cac ttc atg aag ttt ccc acc ggc ttt        167
   Met Tyr Gly Asn Tyr Ser His Phe Met Lys Phe Pro Thr Gly Phe
     1               5                   10                  15 ggt ggc tcc cct ggt cac act ggc tcg acg tcc atg agc cct tca gta        215
Gly Gly Ser Pro Gly His Thr Gly Ser Thr Ser Met Ser Pro Ser Val
                20                  25                  30 gcc ttg ccc acg ggg aag cca atg gac agc cac ccc agc tac aca gac        263
Ala Leu Pro Thr Gly Lys Pro Met Asp Ser His Pro Ser Tyr Thr Asp
            35                  40                  45 acc cca gtg agt gcc cct cgg acg ctg agt gct gtg gga acc ccc ctc        311
Thr Pro Val Ser Ala Pro Arg Thr Leu Ser Ala Val Gly Thr Pro Leu
        50                  55                  60 aat gct ctt ggc tct ccg tat aga gtc atc act tct gcc atg ggt cca        359
Asn Ala Leu Gly Ser Pro Tyr Arg Val Ile Thr Ser Ala Met Gly Pro
    65                  70                  75 ccc tca gga gca ctg gca gct cct cca gga atc aac ttg gtg gct cca        407
Pro Ser Gly Ala Leu Ala Ala Pro Pro Gly Ile Asn Leu Val Ala Pro
 80                  85                  90                  95 ccc agc tcc cag cta aat gtg gtc aac agt gtc agc agc tct gag gac        455
Pro Ser Ser Gln Leu Asn Val Val Asn Ser Val Ser Ser Ser Glu Asp
                100                 105                 110
```

```
atc aag ccc tta cca ggt ctg cct ggg att gga aat atg aac tac cca        503
Ile Lys Pro Leu Pro Gly Leu Pro Gly Ile Gly Asn Met Asn Tyr Pro
            115                 120                 125 tcc acc agc cct ggg tct ctg gtg aaa cac atc tgt gcc atc tgt ggg        551
Ser Thr Ser Pro Gly Ser Leu Val Lys His Ile Cys Ala Ile Cys Gly
        130                 135                 140 gac aga tcc tca ggg aag cac tac ggt gtg tac agc tgt gaa ggt tgc        599
Asp Arg Ser Ser Gly Lys His Tyr Gly Val Tyr Ser Cys Glu Gly Cys
    145                 150                 155 aaa ggc ttc ttc aaa agg acc atc agg aaa gat ctc atc tac acc tgt        647
Lys Gly Phe Phe Lys Arg Thr Ile Arg Lys Asp Leu Ile Tyr Thr Cys
160                 165                 170                 175 cgg gat aac aaa gat tgt ctc atc gac aag cgc cag cgc aac cgc tgc        695
Arg Asp Asn Lys Asp Cys Leu Ile Asp Lys Arg Gln Arg Asn Arg Cys
            180                 185                 190 cag tac tgt cgc tac cag aag tgc ctg gtc atg ggc atg aag cgg gaa        743
Gln Tyr Cys Arg Tyr Gln Lys Cys Leu Val Met Gly Met Lys Arg Glu
        195                 200                 205 gct gtg caa gaa gaa agg cag agg agc cga gag cga gca gag agt gag        791
Ala Val Gln Glu Glu Arg Gln Arg Ser Arg Glu Arg Ala Glu Ser Glu
    210                 215                 220 gca gaa tgt gcc agt agt agc cac gaa gac atg ccc gtg gag agg att        839
Ala Glu Cys Ala Ser Ser Ser His Glu Asp Met Pro Val Glu Arg Ile
225                 230                 235 cta gaa gcc gaa ctt gct gtg gaa cca aag aca gaa tcc tac ggt gac        887
Leu Glu Ala Glu Leu Ala Val Glu Pro Lys Thr Glu Ser Tyr Gly Asp
240                 245                 250                 255 atg aac gtg gag aac tca aca aat gac cct gtt acc aac ata tgc cat        935
Met Asn Val Glu Asn Ser Thr Asn Asp Pro Val Thr Asn Ile Cys His
            260                 265                 270 gct gca gat aag caa ctt ttc acc ctc gtt gag tgg gcc aaa cgc atc        983
Ala Ala Asp Lys Gln Leu Phe Thr Leu Val Glu Trp Ala Lys Arg Ile
        275                 280                 285 ccc cac ttc tca gat ctc acc ttg gag gac cag gtc att cta ctc cgg       1031
Pro His Phe Ser Asp Leu Thr Leu Glu Asp Gln Val Ile Leu Leu Arg
    290                 295                 300 gca ggg tgg aat gaa ctg ctc att gcc tcc ttc tcc cac cgc tcg gtt       1079
Ala Gly Trp Asn Glu Leu Leu Ile Ala Ser Phe Ser His Arg Ser Val
305                 310                 315 tcc gtc cag gat ggc atc ctg ctg gcc acg ggc ctc cac gtg cac agg       1127
Ser Val Gln Asp Gly Ile Leu Leu Ala Thr Gly Leu His Val His Arg
320                 325                 330                 335 agc agc gct cac agc cgg gga gtc ggc tcc atc ttc gac aga gtc ctt       1175
Ser Ser Ala His Ser Arg Gly Val Gly Ser Ile Phe Asp Arg Val Leu
            340                 345                 350 aca gag ttg gtg tcc aag atg aaa gac atg cag atg gat aag tca gag       1223
Thr Glu Leu Val Ser Lys Met Lys Asp Met Gln Met Asp Lys Ser Glu
        355                 360                 365 ctg ggg tgc cta cgg gcc atc gtg ctg ttt aac cca gat gcc aag ggt       1271
Leu Gly Cys Leu Arg Ala Ile Val Leu Phe Asn Pro Asp Ala Lys Gly
    370                 375                 380 tta tcc aac ccc tct gag gtg gag act ctt cga gag aag gtt tat gcc       1319
Leu Ser Asn Pro Ser Glu Val Glu Thr Leu Arg Glu Lys Val Tyr Ala
385                 390                 395 acc ctg gag gcc tat acc aag cag aag tat ccg gaa cag cca ggc agg       1367
Thr Leu Glu Ala Tyr Thr Lys Gln Lys Tyr Pro Glu Gln Pro Gly Arg
400                 405                 410                 415 ttt gcc aag ctt ctg ctg cgt ctc cct gct ctg cgc tcc atc ggc ttg       1415
Phe Ala Lys Leu Leu Leu Arg Leu Pro Ala Leu Arg Ser Ile Gly Leu
            420                 425                 430
```

```
aaa tgc ctg gaa cac ctc ttc ttc aag ctc att gga gac act ccc    1463
Lys Cys Leu Glu His Leu Phe Phe Lys Leu Ile Gly Asp Thr Pro
        435                 440                 445 atc gac agc ttc ctc atg gag atg ttg gag acc cca ctg cag atc acc    1511
Ile Asp Ser Phe Leu Met Glu Met Leu Glu Thr Pro Leu Gln Ile Thr
        450                 455                 460 tgaacctcct cagctgcagc ttccccaccc agggtgaccc ttgggcgggt gtgtgtgtgt    1571
ggccctaccc tgcacactct cccccatctt ccactctggc ctcccttcct gtcccaaaa     1631 tgtgatgctt gtaataagcg gccgcgaatt c                                   1662

<210> SEQ ID NO 6
<211> LENGTH: 463
<212> TYPE: PRT
<213> ORGANISM: Mus sp.

<400> SEQUENCE: 6

Met Tyr Gly Asn Tyr Ser His Phe Met Lys Phe Pro Thr Gly Phe Gly
 1               5                  10                  15

Gly Ser Pro Gly His Thr Gly Ser Thr Ser Met Ser Pro Ser Val Ala
            20                  25                  30

Leu Pro Thr Gly Lys Pro Met Asp Ser His Pro Ser Tyr Thr Asp Thr
        35                  40                  45

Pro Val Ser Ala Pro Arg Thr Leu Ser Ala Val Gly Thr Pro Leu Asn
    50                  55                  60

Ala Leu Gly Ser Pro Tyr Arg Val Ile Thr Ser Ala Met Gly Pro Pro
65                  70                  75                  80

Ser Gly Ala Leu Ala Ala Pro Gly Ile Asn Leu Val Ala Pro Pro
                85                  90                  95

Ser Ser Gln Leu Asn Val Val Asn Ser Val Ser Ser Glu Asp Ile
            100                 105                 110

Lys Pro Leu Pro Gly Leu Pro Gly Ile Gly Asn Met Asn Tyr Pro Ser
            115                 120                 125

Thr Ser Pro Gly Ser Leu Val Lys His Ile Cys Ala Ile Cys Gly Asp
        130                 135                 140

Arg Ser Ser Gly Lys His Tyr Gly Val Tyr Ser Cys Glu Gly Cys Lys
145                 150                 155                 160

Gly Phe Phe Lys Arg Thr Ile Arg Lys Asp Leu Ile Tyr Thr Cys Arg
                165                 170                 175

Asp Asn Lys Asp Cys Leu Ile Asp Lys Arg Gln Arg Asn Arg Cys Gln
            180                 185                 190

Tyr Cys Arg Tyr Gln Lys Cys Leu Val Met Gly Met Lys Arg Glu Ala
        195                 200                 205

Val Gln Glu Glu Arg Gln Arg Ser Arg Glu Arg Ala Glu Ser Glu Ala
    210                 215                 220

Glu Cys Ala Ser Ser Ser His Glu Asp Met Pro Val Glu Arg Ile Leu
225                 230                 235                 240

Glu Ala Glu Leu Ala Val Glu Pro Lys Thr Glu Ser Tyr Gly Asp Met
                245                 250                 255

Asn Val Glu Asn Ser Thr Asn Asp Pro Val Thr Asn Ile Cys His Ala
            260                 265                 270

Ala Asp Lys Gln Leu Phe Thr Leu Val Glu Trp Ala Lys Arg Ile Pro
        275                 280                 285

His Phe Ser Asp Leu Thr Leu Glu Asp Gln Val Ile Leu Leu Arg Ala
    290                 295                 300
```

-continued

```
Gly Trp Asn Glu Leu Leu Ile Ala Ser Phe Ser His Arg Ser Val Ser
305                 310                 315                 320

Val Gln Asp Gly Ile Leu Leu Ala Thr Gly Leu His Val His Arg Ser
            325                 330                 335

Ser Ala His Ser Arg Gly Val Gly Ser Ile Phe Asp Arg Val Leu Thr
            340                 345                 350

Glu Leu Val Ser Lys Met Lys Asp Met Gln Met Asp Lys Ser Glu Leu
            355                 360                 365

Gly Cys Leu Arg Ala Ile Val Leu Phe Asn Pro Asp Ala Lys Gly Leu
370                 375                 380

Ser Asn Pro Ser Glu Val Glu Thr Leu Arg Glu Lys Val Tyr Ala Thr
385                 390                 395                 400

Leu Glu Ala Tyr Thr Lys Gln Lys Tyr Pro Glu Gln Pro Gly Arg Phe
            405                 410                 415

Ala Lys Leu Leu Leu Arg Leu Pro Ala Leu Arg Ser Ile Gly Leu Lys
            420                 425                 430

Cys Leu Glu His Leu Phe Phe Phe Lys Leu Ile Gly Asp Thr Pro Ile
            435                 440                 445

Asp Ser Phe Leu Met Glu Met Leu Glu Thr Pro Leu Gln Ile Thr
    450                 455                 460

<210> SEQ ID NO 7
<211> LENGTH: 2219
<212> TYPE: DNA
<213> ORGANISM: Mus musculus
<220> FEATURE:
<221> NAME/KEY: CDS
<222> LOCATION: (109)..(1338)

<400> SEQUENCE: 7
gaattccccc gaagcccaga cagctcctcc ccaaatcccc tttctcaggg gatccgtccg      60
tcttctcctc ctggcccacc tcttacccct tcagcacctc cacctcca atg cca ccc     117
                                                     Met Pro Pro
                                                       1 ccg cca ctg ggc tcc ccc ttc cca gtc atc agt tct tcc atg ggg tcc     165
Pro Pro Leu Gly Ser Pro Phe Pro Val Ile Ser Ser Ser Met Gly Ser
    5                  10                  15 cct ggt ctg ccc cct ccg gct ccc cca gga ttc tcc ggg cct gtc agc     213
Pro Gly Leu Pro Pro Pro Ala Pro Pro Gly Phe Ser Gly Pro Val Ser
20                  25                  30                  35 agc cct cag atc aac tcc aca gtg tcg ctc cct ggg ggt ggg tct ggc     261
Ser Pro Gln Ile Asn Ser Thr Val Ser Leu Pro Gly Gly Gly Ser Gly
                40                  45                  50 ccc cct gaa gat gtg aag cca ccg gtc tta ggg gtc cgg ggc ctg cac     309
Pro Pro Glu Asp Val Lys Pro Pro Val Leu Gly Val Arg Gly Leu His
            55                  60                  65 tgt cca ccc cct cca ggt ggt cct ggg gct ggc aaa cgg ctc tgt gca     357
Cys Pro Pro Pro Pro Gly Gly Pro Gly Ala Gly Lys Arg Leu Cys Ala
        70                  75                  80 atc tgc ggg gac cga agc tca ggc aag cac tat ggg gtt tac agc tgc     405
Ile Cys Gly Asp Arg Ser Ser Gly Lys His Tyr Gly Val Tyr Ser Cys
    85                  90                  95 gag ggc tgc aag ggt ttc ttc aag cgc acc att cgg aag gac ctg acc     453
Glu Gly Cys Lys Gly Phe Phe Lys Arg Thr Ile Arg Lys Asp Leu Thr
100                 105                 110                 115 tac tcg tgt cgt gat aac aaa gac tgt aca gtg gac aag cgc cag cgg     501
Tyr Ser Cys Arg Asp Asn Lys Asp Cys Thr Val Asp Lys Arg Gln Arg
                120                 125                 130
```

```
aat cgc tgt cag tac tgt cgc tat cag aag tgc ctg gcc act ggc atg        549
Asn Arg Cys Gln Tyr Cys Arg Tyr Gln Lys Cys Leu Ala Thr Gly Met
         135                 140                 145 aaa agg gag gcg gtt cag gag gag cgt caa cgg ggg aag gac aaa gac        597
Lys Arg Glu Ala Val Gln Glu Glu Arg Gln Arg Gly Lys Asp Lys Asp
    150                 155                 160 ggg gat gga gat ggg gct ggg gga gcc cct gag gag atg cct gtg gac        645
Gly Asp Gly Asp Gly Ala Gly Gly Ala Pro Glu Glu Met Pro Val Asp
    165                 170                 175 agg atc ctg gag gca gag ctt gct gtg gag cag aag agt gac caa ggc        693
Arg Ile Leu Glu Ala Glu Leu Ala Val Glu Gln Lys Ser Asp Gln Gly
180                 185                 190                 195 gtt gag ggt cct ggg gcc acc ggg ggt ggt ggc agc agc cca aat gac        741
Val Glu Gly Pro Gly Ala Thr Gly Gly Gly Gly Ser Ser Pro Asn Asp
                200                 205                 210 cca gtg act aac atc tgc cag gca gct gac aaa cag ctg ttc aca ctc        789
Pro Val Thr Asn Ile Cys Gln Ala Ala Asp Lys Gln Leu Phe Thr Leu
                215                 220                 225 gtt gag tgg gca aag agg atc ccg cac ttc tcc tcc cta cct ctg gac        837
Val Glu Trp Ala Lys Arg Ile Pro His Phe Ser Ser Leu Pro Leu Asp
            230                 235                 240 gat cag gtc ata ctg ctg cgg gca ggc tgg aac gag ctc ctc att gcg        885
Asp Gln Val Ile Leu Leu Arg Ala Gly Trp Asn Glu Leu Leu Ile Ala
            245                 250                 255 tcc ttc tcc cat cgg tcc att gat gtc cga gat ggc atc ctc ctg gcc        933
Ser Phe Ser His Arg Ser Ile Asp Val Arg Asp Gly Ile Leu Leu Ala
260                 265                 270                 275 acg ggt ctt cat gtg cac aga aac tca gcc cat tcc gca ggc gtg gga        981
Thr Gly Leu His Val His Arg Asn Ser Ala His Ser Ala Gly Val Gly
                280                 285                 290 gcc atc ttt gat cgg gtg ctg aca gag cta gtg tcc aaa atg cgt gac       1029
Ala Ile Phe Asp Arg Val Leu Thr Glu Leu Val Ser Lys Met Arg Asp
                295                 300                 305 atg agg atg gac aag aca gag ctt ggc tgc ctg cgg gca atc ata ctg       1077
Met Arg Met Asp Lys Thr Glu Leu Gly Cys Leu Arg Ala Ile Ile Leu
            310                 315                 320 ttt aat cca gac gcc aag ggc ctc tcc aac cct gga gag gtg gag atc       1125
Phe Asn Pro Asp Ala Lys Gly Leu Ser Asn Pro Gly Glu Val Glu Ile
            325                 330                 335 ctt cgg gag aag gtg tac gcc tca ctg gag acc tat tgc aag cag aag       1173
Leu Arg Glu Lys Val Tyr Ala Ser Leu Glu Thr Tyr Cys Lys Gln Lys
340                 345                 350                 355 tac cct gag cag cag ggc cgg ttt gcc aag ctg ctg tta cgt ctt cct       1221
Tyr Pro Glu Gln Gln Gly Arg Phe Ala Lys Leu Leu Leu Arg Leu Pro
                360                 365                 370 gcc ctc cgc tcc atc ggc ctc aag tgt ctg gag cac ctg ttc ttc ttc       1269
Ala Leu Arg Ser Ile Gly Leu Lys Cys Leu Glu His Leu Phe Phe Phe
                375                 380                 385 aag ctc att ggc gac acc ccc att gac acc ttc ctc atg gag atg ctt       1317
Lys Leu Ile Gly Asp Thr Pro Ile Asp Thr Phe Leu Met Glu Met Leu
            390                 395                 400 gag gct ccc cac cag cta gcc tgagcccaga tgcacaccga gtgtcactga          1368
Glu Ala Pro His Gln Leu Ala
405                 410 ggaggacttg agcctgggca gggggcagag ccatgggaca ggtgcagagc aggaggggac     1428
ttgcccagcc tgccagggat ctggcaacac ttagcagggt tcgcttggtc tccaagtcga     1488
aggggacccc agatccctgt gaggacttta tgtctacctt cagtggcctt gagtctctga     1548
```

-continued

```
atttgtcggg gtctcccatg gtgcaggtga ttcttcatcc tggctcccca gcacaaagca    1608
ctgccctgct tccttctcat ttggcctcac tcccttctga agagtggaac agagctcccc    1668
cagaaagggg tgttgtgggg caggcccccc aagctgatga tcatgggagc agggctctga    1728
cagcctttat cctctcagac ttgacagatg ggggcagagg agggacctgc ctctgtctcc    1788
tgtcagcccc atttccacag tccctcctgc agtcagactg aagaataaag gggtagtgaa    1848
ggggctgctg gaggtggagg aacccattgc tcttttaatt tcctgtgagg agagactggg    1908
agttagactc aaagaagtac tgtacatccc caggttgact taaatgtcag ggctggagat    1968
ggcatgtggg caaggaggcc cctcaggtgg gctgtcccaa agctccctgg gctctgcctc    2028
gggtggccct acagctcttc cctagtctta agcacagcta ggctgggagc aagtggggac    2088
attgatgggg gtggccagcc tgcagagttg ggtgctgggc tgcatggttt ttgccctgga    2148
cctcttttgg gggttccctc ccatctttca cttgcacata aagttgcttt ccagttaaaa    2208
aaaaaaaaaa a                                                          2219
```

<210> SEQ ID NO 8
<211> LENGTH: 410
<212> TYPE: PRT
<213> ORGANISM: Mus musculus

<400> SEQUENCE: 8

```
Met Pro Pro Pro Pro Leu Gly Ser Pro Phe Pro Val Ile Ser Ser
 1               5                  10                  15

Met Gly Ser Pro Gly Leu Pro Pro Ala Pro Pro Gly Phe Ser Gly
            20                  25                  30

Pro Val Ser Ser Pro Gln Ile Asn Ser Thr Val Ser Leu Pro Gly Gly
        35                  40                  45

Gly Ser Gly Pro Pro Glu Asp Val Lys Pro Pro Val Leu Gly Val Arg
    50                  55                  60

Gly Leu His Cys Pro Pro Pro Gly Gly Pro Gly Ala Gly Lys Arg
 65                  70                  75                  80

Leu Cys Ala Ile Cys Gly Asp Arg Ser Ser Gly Lys His Tyr Gly Val
                85                  90                  95

Tyr Ser Cys Glu Gly Cys Lys Gly Phe Phe Lys Arg Thr Ile Arg Lys
            100                 105                 110

Asp Leu Thr Tyr Ser Cys Arg Asp Asn Lys Asp Cys Thr Val Asp Lys
        115                 120                 125

Arg Gln Arg Asn Arg Cys Gln Tyr Cys Arg Tyr Gln Lys Cys Leu Ala
    130                 135                 140

Thr Gly Met Lys Arg Glu Ala Val Gln Glu Glu Arg Gln Arg Gly Lys
145                 150                 155                 160

Asp Lys Asp Gly Asp Gly Asp Gly Ala Gly Gly Ala Pro Glu Glu Met
                165                 170                 175

Pro Val Asp Arg Ile Leu Glu Ala Glu Leu Ala Val Glu Gln Lys Ser
            180                 185                 190

Asp Gln Gly Val Glu Gly Pro Gly Ala Thr Gly Gly Gly Ser Ser
        195                 200                 205

Pro Asn Asp Pro Val Thr Asn Ile Cys Gln Ala Ala Asp Lys Gln Leu
    210                 215                 220

Phe Thr Leu Val Glu Trp Ala Lys Arg Ile Pro His Phe Ser Ser Leu
225                 230                 235                 240

Pro Leu Asp Asp Gln Val Ile Leu Leu Arg Ala Gly Trp Asn Glu Leu
                245                 250                 255
```

```
Leu Ile Ala Ser Phe Ser His Arg Ser Ile Asp Val Arg Asp Gly Ile
        260                 265                 270
Leu Leu Ala Thr Gly Leu His Val His Arg Asn Ser Ala His Ser Ala
    275                 280                 285
Gly Val Gly Ala Ile Phe Asp Arg Val Leu Thr Glu Leu Val Ser Lys
    290                 295                 300
Met Arg Asp Met Arg Met Asp Lys Thr Glu Leu Gly Cys Leu Arg Ala
305                 310                 315                 320
Ile Ile Leu Phe Asn Pro Asp Ala Lys Gly Leu Ser Asn Pro Gly Glu
                325                 330                 335
Val Glu Ile Leu Arg Glu Lys Val Tyr Ala Ser Leu Glu Thr Tyr Cys
            340                 345                 350
Lys Gln Lys Tyr Pro Glu Gln Gln Gly Arg Phe Ala Lys Leu Leu Leu
        355                 360                 365
Arg Leu Pro Ala Leu Arg Ser Ile Gly Leu Lys Cys Leu Glu His Leu
    370                 375                 380
Phe Phe Phe Lys Leu Ile Gly Asp Thr Pro Ile Asp Thr Phe Leu Met
385                 390                 395                 400
Glu Met Leu Glu Ala Pro His Gln Leu Ala
                405                 410

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide linker

<400> SEQUENCE: 9
gatccgatat ccatatggaa ttcggtacca                                    30

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aggtcatgac ct                                                       12

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctagaggtca tgacct                                                   16

<210> SEQ ID NO 12
<211> LENGTH: 16
```

```
-continued
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ctagaggtca tgacct                                                     16
```